(12) United States Patent
Shiraishi

(10) Patent No.: US 10,463,240 B2
(45) Date of Patent: Nov. 5, 2019

(54) ENDOSCOPE SYSTEM, PROCESSOR DEVICE, OPERATION METHOD, AND DISTANCE MEASUREMENT DEVICE

(71) Applicant: FUJIFILM Corporation, Tokyo (JP)

(72) Inventor: Yasushi Shiraishi, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 728 days.

(21) Appl. No.: 15/063,776

(22) Filed: Mar. 8, 2016

(65) Prior Publication Data

US 2016/0183774 A1  Jun. 30, 2016

Related U.S. Application Data

(63) Continuation of application No. PCT/JP2014/072186, filed on Aug. 25, 2014.

(30) Foreign Application Priority Data

Sep. 27, 2013 (JP) ................................. 2013-202544

(51) Int. Cl.
   *A61B 1/00* (2006.01)
   *A61B 1/04* (2006.01)
   (Continued)

(52) U.S. Cl.
   CPC .......... *A61B 1/043* (2013.01); *A61B 1/00009* (2013.01); *A61B 1/0638* (2013.01);
   (Continued)

(58) Field of Classification Search
   CPC .............................. A61B 1/043; A61B 1/3137
   (Continued)

(56) References Cited

U.S. PATENT DOCUMENTS 5,784,098 A   7/1998 Shoji et al.
8,390,679 B2  3/2013 Uchiyama et al.
(Continued)

FOREIGN PATENT DOCUMENTS

JP      9-294708 A    11/1997
JP   2003-36436 A     2/2003
(Continued)

OTHER PUBLICATIONS

Japanese Office Action for Japanese Application No. 2013-202544, dated Oct. 26, 2016, with Machine translation.
(Continued)

*Primary Examiner* — Alexandra L Newton
*Assistant Examiner* — Rynae Boler
(74) *Attorney, Agent, or Firm* — Birch, Stewart, Kolasch & Birch, LLP

(57) ABSTRACT

There are provided an endoscope system, a processor device, an operation method, and a distance measurement device for accurately measuring the observation distance even if a colorant or residues are present in a subject. An endoscope system 10 includes a light source device 14, an endoscope 12, and an observation distance measurement unit 63. The light source device 14 emits signal light, which has a wavelength band absorbed by hemoglobin contained in the subject, to the subject. The endoscope 12 has an image sensor 48 that images the subject with reflected light of the signal light and outputs an image signal. The observation distance measurement unit 63 measures the observation distance based on the image signal.

17 Claims, 22 Drawing Sheets

(51) Int. Cl.
- *A61B 1/06* (2006.01)
- *A61B 1/313* (2006.01)
- *A61B 5/1459* (2006.01)
- *A61B 5/145* (2006.01)
- *A61B 5/1455* (2006.01)

(52) U.S. Cl.
CPC .......... *A61B 1/0661* (2013.01); *A61B 1/0684* (2013.01); *A61B 1/3137* (2013.01); *A61B 5/1459* (2013.01); *A61B 1/0653* (2013.01); *A61B 5/14546* (2013.01); *A61B 5/14556* (2013.01)

(58) Field of Classification Search
USPC ......................................................... 600/317
See application file for complete search history.

(56) References Cited

U.S. PATENT DOCUMENTS

| | | | |
|---|---|---|---|
| 2002/0168096 A1 | 11/2002 | Hakamata et al. | |
| 2006/0025692 A1 | 2/2006 | Ishihara | |
| 2009/0322863 A1* | 12/2009 | Takahashi | G01C 3/00 348/65 |
| 2011/0237884 A1* | 9/2011 | Saito | A61B 1/00009 600/109 |
| 2011/0273548 A1 | 11/2011 | Uchiyama et al. | |
| 2012/0302847 A1 | 11/2012 | Ozawa et al. | |
| 2013/0286172 A1* | 10/2013 | Sasaki | A61B 1/00009 348/65 |
| 2015/0363929 A1* | 12/2015 | Higuchi | A61B 1/0646 382/128 |

FOREIGN PATENT DOCUMENTS

| | | |
|---|---|---|
| JP | 2006-61683 A | 3/2006 |
| JP | 2012-239816 A | 12/2012 |
| JP | 2013-146484 A | 8/2013 |
| WO | WO 2010/143692 A1 | 12/2010 |

OTHER PUBLICATIONS

English translation of International Preliminary Report on patentability for PCT/JP2014/072186 (PCT/IPEA/409) dated Jan. 29, 2016.
Extended European Search Report for European Application No. 14848180.7, dated Aug. 5, 2016.
International Preliminary Report on patentability for PCT/JP2014/072186 (PCT/IPEA/409) dated Oct. 20, 2015.
International Search Report for PCT/JP2014/072186 (PCT/ISA/210) dated Nov. 18, 2014.
Written Opinion of the International Searching Authority for PCT/JP2014/072186 (PCT/ISA/237) dated Nov. 18, 2014.

* cited by examiner

| ΔBG, ΔGR, ΔRB | OBSERVATION DISTANCE |
|---|---|
| k101, k102, k103 | 8.2 mm |
| k104, k105, k106 | 3.7 mm |
| k107, k108, k109 | 1.2 mm |
| ⋮ | ⋮ |

83b

| OBSERVATION DISTANCE | ERROR OF OXYGEN SATURATION |
|---|---|
| 10.5 mm | +10% |
| 8.2 mm | ±0% |
| 2.5 mm | −2% |
| ⋮ | ⋮ |

| ΔBG, ΔGR, ΔRB | OBSERVATION DISTANCE | ERROR OF OXYGEN SATURATION |
|---|---|---|
| k1, k2, k3 | 10.5 mm | +10% |
| k4, k5, k6 | 8.2 mm | ±0% |
| k7, k8, k9 | 2.5 mm | −2% |
| ⋮ | ⋮ | ⋮ |

ENDOSCOPE SYSTEM, PROCESSOR DEVICE, OPERATION METHOD, AND DISTANCE MEASUREMENT DEVICE

CROSS-REFERENCE TO RELATED APPLICATIONS

This application is a Continuation of PCT International Application No. PCT/JP2014/072186 filed on Aug. 25, 2014, which claims priority under 35 U.S.C § 119(a) to Japanese Patent Application No. 2013-202544 filed on Sep. 27, 2013. Each of the above application(s) is hereby expressly incorporated by reference, in its entirety, into the present application.

BACKGROUND OF THE INVENTION

1. Field of the Invention

The present invention relates to an endoscope system, a processor device, an operation method, and a distance measurement device for observing the inside of a subject.

2. Description of the Related Art

In the medical field, it is common to perform diagnosis using an endoscope system. The endoscope system includes a light source device that generates light for irradiating a subject, an endoscope that images the subject, and a processor device that performs processing on an image signal obtained by imaging the subject, for example.

In the case of observing the subject using the endoscope system, there is a desire to know a distance between the subject and a distal portion of the endoscope (hereinafter, referred to as an observation distance) for various reasons. For example, in the endoscope system disclosed in JP1997-294708A (JP-H09-294708A), an interferometer is provided in an endoscope in order to prevent a subject from being damaged by contact with the distal portion, and the observation distance is measured using the interferometer.

SUMMARY OF THE INVENTION

In a case in which the interferometer for measuring the observation distance is provided as disclosed in JP1997-294708A (JP-H09-294708A), there is a problem that the cost is increased. In addition, in the endoscope system disclosed in JP1997-294708A (JP-H09-294708A), space for placing a member that forms the interferometer is required even though it is difficult for the insertion unit of the endoscope to have a large diameter. Accordingly, since the internal space of each unit of the endoscope system is compressed, the degree of freedom in design is reduced. For example, in the case of providing the interferometer for measuring the observation distance, size reduction and space saving are difficult compared with a case in which the interferometer is not present.

It is an object of the present invention to provide an endoscope system, a processor device, an operation method, and a distance measurement device that can measure the observation distance without adding an interferometer or the like.

An endoscope system of the present invention includes a light source device, an endoscope, and an observation distance measurement unit. The light source device emits signal light, which has a wavelength band absorbed by hemoglobin contained in a subject, to the subject. The endoscope has an image sensor that images the subject by receiving reflected light of the signal light and outputs an image signal. The observation distance measurement unit measures an observation distance based on the image signal.

Preferably, the observation distance measurement unit can perform switching between a first measurement mode to measure the observation distance in a case in which a non-hemoglobin substance that changes an amount of reflection of the signal light by the subject is not present other than hemoglobin contained in the subject and a second measurement mode to measure the observation distance in a case in which the non-hemoglobin substance is present, and calculates the observation distance in one of the first and second measurement modes.

The observation distance measurement unit includes a frequency component information extraction section that extracts frequency component information from the image signal and an observation distance calculation section that calculates the observation distance based on the frequency component information of the image signal.

The frequency component information is, for example, the amplitude of a specific frequency component. In the case of using the amplitude of a specific frequency component as frequency component information, the observation distance calculation section calculates the observation distance, for example, based on a difference between the amplitudes extracted for two image signals having different corresponding wavelength bands (colors of R, B, and the like). In addition, the specific frequency component is information regarding a frequency component corresponding to the superficial blood vessel of the subject.

For example, the observation distance calculation section has a first distance table, in which the frequency component information in a case in which the non-hemoglobin substance is not present is associated with the observation distance, and a second distance table, in which the frequency component information in a case in which the non-hemoglobin substance is present is associated with the observation distance. In the first measurement mode, the observation distance is calculated using the first distance table. In the second measurement mode, the observation distance is calculated using the second distance table.

The observation distance calculation section may calculate the observation distance using a function of associating the frequency component information with the observation distance. In this case, as the function of associating the frequency component information with the observation distance, a first distance calculation function for the first measurement mode and a second distance calculation function for the second measurement mode are provided.

A non-hemoglobin substance introduction unit that introduces the non-hemoglobin substance may be provided. The non-hemoglobin substance introduction unit is, for example, a forceps channel.

The non-hemoglobin substance is a colorant for coloring the subject and/or a cleaning agent for cleaning the inside of the subject. The colorant contains at least one of indigo carmine, toluidine blue, methylene blue, compound iodine glycerin, crystal violet, fluorescein, acridine orange, indocyanine green, and acetic acid, for example. Alternatively, the non-hemoglobin substance may be residues remaining in the subject and/or secretions secreted by the subject.

The observation distance is a distance between a distal portion of the endoscope and the subject. In a case in which the endoscope includes a zoom lens for magnifying an image that is formed on the image sensor by reflected light of first signal light and reflected light of second signal light, the observation distance is a distance based on the magnification of the image by the zoom lens.

It is preferable that the observation distance calculation section divides the image signal into a plurality of regions, and calculates the observation distance for each of the regions.

In the endoscope system of the present invention, preferably, the light source device emits first signal light and second signal light having different wavelength bands to the subject as the signal light, and the image sensor images the subject by receiving reflected light of the first signal light and reflected light of the second signal light, and outputs a first image signal and a second image signal. It is preferable to further include an oxygen saturation calculation unit that calculates an oxygen saturation of the subject for each pixel based on a signal ratio between the first image signal and the second image signal output from the same pixel, a correction unit that corrects the oxygen saturation based on the observation distance, and an image generation unit that generates an oxygen saturation image showing the oxygen saturation of the subject based on the oxygen saturation corrected by the correction unit.

A processor device of the present invention is a processor device for an endoscope system including a light source device that emits signal light, which has a wavelength band absorbed by hemoglobin contained in a subject, to the subject, and an endoscope having an image sensor that images the subject by receiving reflected light of the signal light and outputs an image signal, and includes an observation distance measurement unit. The observation distance measurement unit measures an observation distance of the subject by the endoscope based on the image signal.

An operation method of the present invention is an operation method for an endoscope system including a light source device that emits signal light, which has a wavelength band absorbed by hemoglobin contained in a subject, to the subject, and an endoscope having an image sensor that images the subject by receiving reflected light of the signal light and outputs an image signal, and includes an observation distance measurement step of measuring an observation distance of the subject by the endoscope based on the image signal.

A distance measurement device of the present invention includes a light source device, an image sensor, and an observation distance measurement unit. The light source device emits signal light, which has a wavelength band absorbed by hemoglobin contained in a subject, to the subject. The image sensor images the subject by receiving reflected light of the signal light and outputs an image signal. The observation distance measurement unit measures the observation distance of the subject based on the image signal.

Since the endoscope system, the processor device, the operation method, and the distance measurement device of the present invention can measure the observation distance based on the image signal output from the image sensor, it is possible to measure the observation distance without adding an interferometer or the like. Therefore, low-cost production is possible, and the degree of freedom in design is not reduced.

BRIEF DESCRIPTION OF THE DRAWINGS

FIG. 21 is an explanatory diagram showing data obtained by observing the phantom.

DESCRIPTION OF THE PREFERRED EMBODIMENTS

First Embodiment

Figure 1:
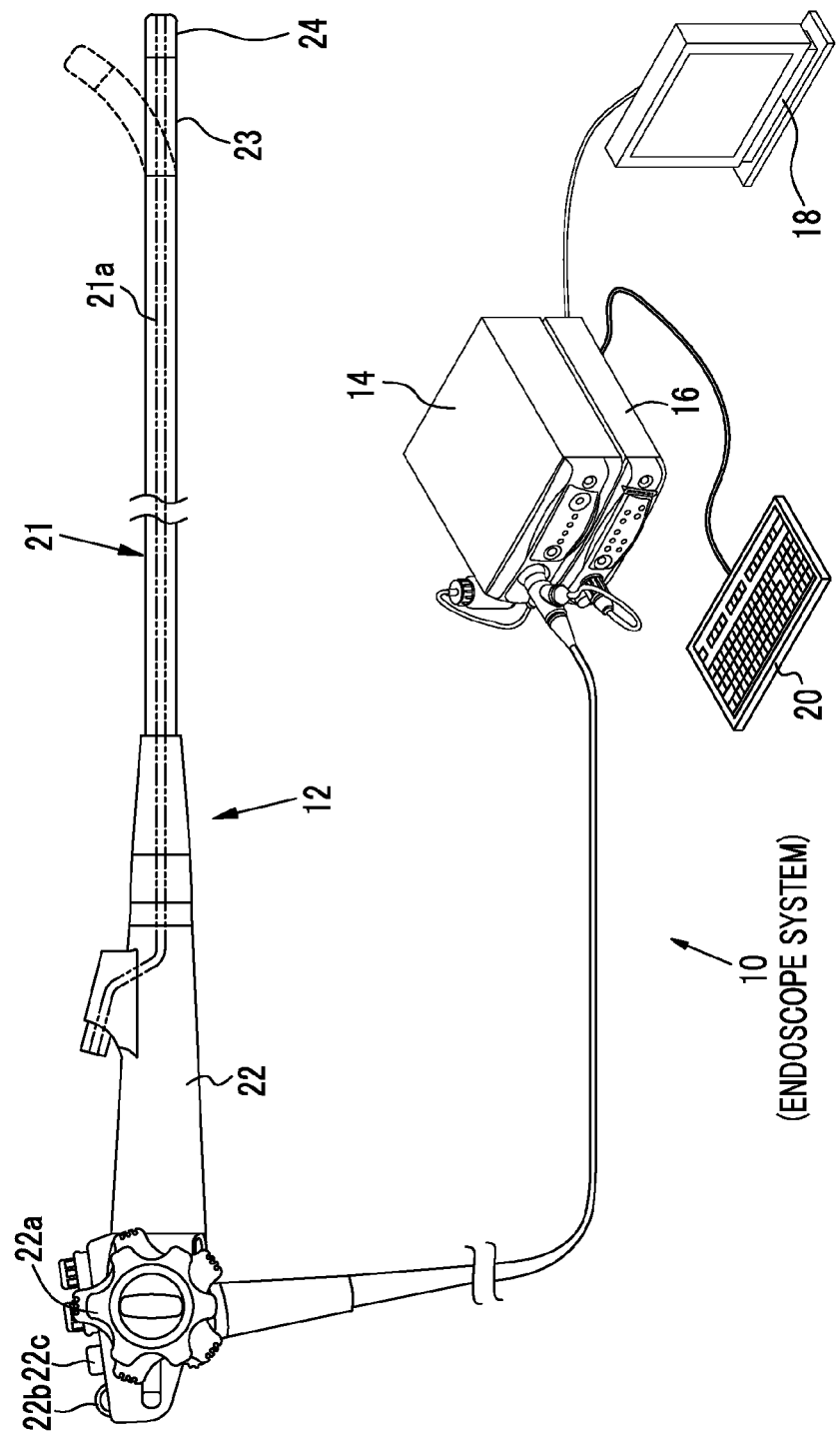
FIG. 1 is an external view of an endoscope system.

As shown in FIG. 1, an endoscope system 10 of a first embodiment includes an endoscope 12, a light source device 14, a processor device 16, a monitor 18, and a console 20. The endoscope 12 is optically connected to the light source device 14, and is electrically connected to the processor device 16. The endoscope 12 includes an insertion unit 21 that is inserted into a subject, an operation unit 22 provided at the proximal end of the insertion unit 21, and a bending portion 23 and a distal portion 24 that are provided at the distal side of the insertion unit 21. By operating an angle knob 22a of the operation unit 22, the bending portion 23 is bent. Through the bending operation, the distal portion 24 is directed toward a desired direction.

A forceps channel 21a for inserting a treatment instrument, such as forceps, is provided in the insertion unit 21. An inlet of the forceps channel 21a is provided in the operation unit 22, and an outlet is provided in the distal portion 24. In the case of introducing a colorant for coloring a specific tissue or the like into the subject in a state in which the insertion unit 21 is inserted into the subject, a treatment instrument (not shown) for introducing the colorant or the like is inserted into the forceps channel 21a, and the colorant or the like is introduced into the subject from the distal portion 24. The forceps channel 21a in this case forms an introduction portion for introducing the colorant or the like.

In addition to the angle knob 22a, a mode selector SW (mode selector switch) 22b and a zoom operation unit 22c are provided in the operation unit 22. The mode selector SW 22b is used for a switching operation between two modes of a normal observation mode and a special observation mode. The normal observation mode is a mode in which a normal light image obtained by full-color imaging of the inside of the subject is displayed on the monitor 18. The special observation mode is a mode in which an oxygen saturation image obtained by imaging the oxygen saturation of blood hemoglobin in the subject is displayed on the monitor 18. The zoom operation unit 22c is used for a zooming operation for driving a zoom lens 47 (refer to FIG. 2) in the endoscope 12 in order to magnify the subject.

The processor device 16 is electrically connected to the monitor 18 and the console 20. The monitor 18 displays an image, such as a normal light image or an oxygen saturation image, and information regarding these images (hereinafter, referred to as image information or the like). The console 20 functions as a user interface (UI) for receiving an input operation, such as a function setting. In addition, a recording unit (not shown) in which image information or the like is recorded may be connected to the processor device 16.

Figure 2:
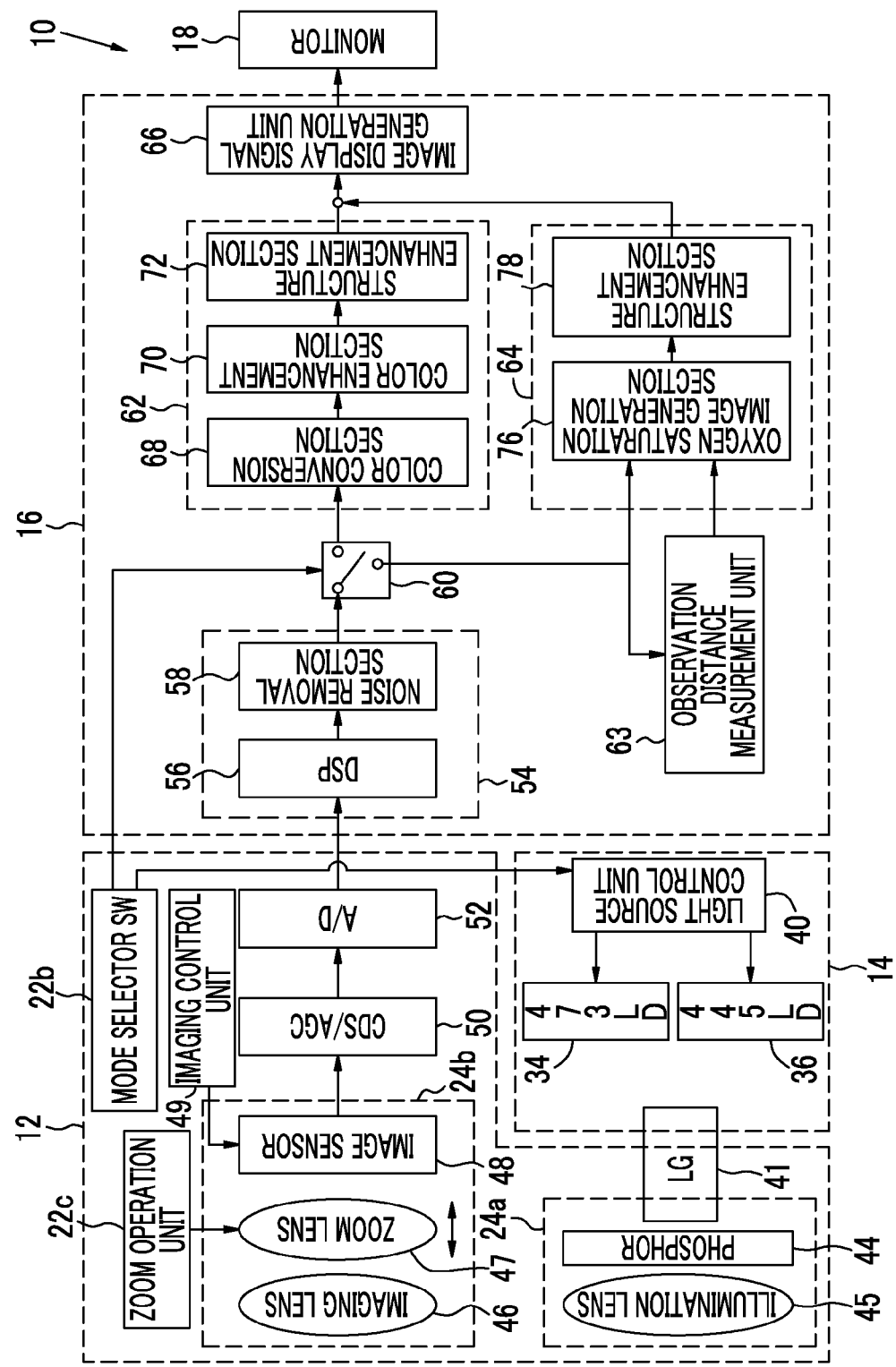
FIG. 2 is a block diagram of the endoscope system.

As shown in FIG. 2, the light source device 14 includes, as light emitting sources, a first blue laser light source (473 LD (laser diode)) 34 that emits first blue laser light having a center wavelength of 473 nm and a second blue laser light source (445 LD) 36 that emits second blue laser light having a center wavelength of 445 nm. Emission of the light sources 34 and 36 formed of semiconductor light emitting devices is individually controlled by a light source control unit 40. Therefore, the light amount ratio between light emitted from the first blue laser light source 34 and light emitted from the second blue laser light source 36 can be freely changed.

In the case of the normal observation mode, the light source control unit 40 turns on the second blue laser light source 36 to emit the second blue laser light. On the other hand, in the case of the special observation mode, the first blue laser light source 34 and the second blue laser light source 36 are alternately turned on at intervals of one frame to alternately emit the first blue laser light and the second blue laser light. In addition, it is preferable that the half-width of each of the first and second blue laser light beams is set to approximately ±10 nm. As the first blue laser light source 34 and the second blue laser light source 36, a broad area type InGaN-based laser diode can be used, or an InGaNAs-based laser diode or a GaNAs-based laser diode can be used. In addition, as the above light sources, a structure using a light emitter, such as a light emitting diode, may be used.

The first and second blue laser light beams emitted from the light sources 34 and 36 are incident on a light guide (LG) 41 through optical members, such as a condensing lens, an optical fiber, and a multiplexer (none are shown). The light guide 41 is built into a universal cord that connects the light source device 14 and the endoscope 12 to each other. The light guide 41 causes the first and second blue laser light beams to propagate from the light sources 34 and 36 to the distal portion 24 of the endoscope 12 therethrough. As the light guide 41, it is possible to use a multi-mode fiber. As an example, it is possible to use a small-diameter fiber cable having a diameter of ϕ0.3 mm to ϕ0.5 mm that includes a core with a diameter of 105 ϕm, a cladding with a diameter of 125 ϕm, and a protective layer as an outer skin.

The distal portion 24 of the endoscope 12 includes an illumination optical system 24a and an imaging optical system 24b. A phosphor 44 and an illumination lens 45 are provided in the illumination optical system 24a. The first and second blue laser light beams are incident on the phosphor 44 from the light guide 41. The phosphor 44 emits fluorescence due to the first or second blue laser light emitted thereto. Some of the first or second blue laser light beams are transmitted through the phosphor 44. The light emitted from the phosphor 44 is emitted to the inside of the subject through the illumination lens 45.

Figure 3:
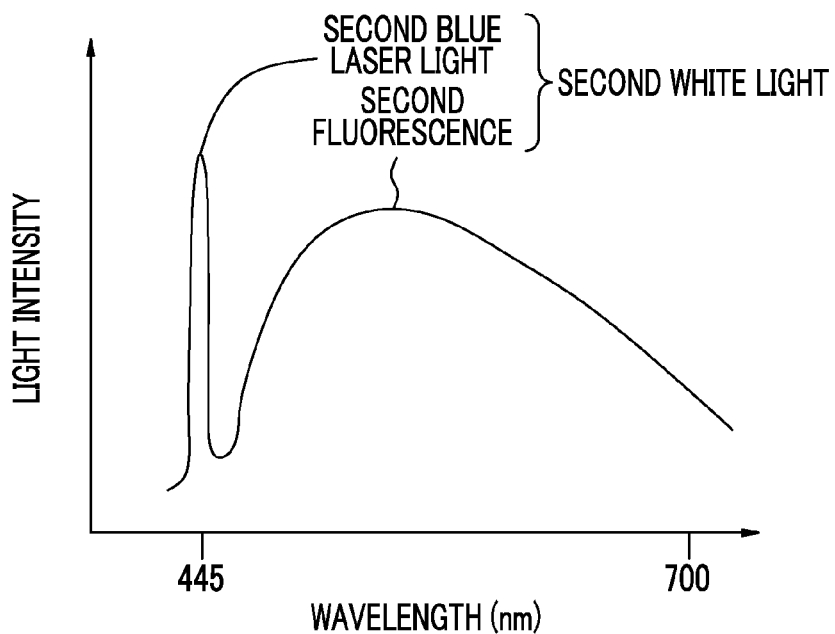
FIG. 3 is a graph showing the spectrum of second white light emitted in a normal observation mode.

In the normal observation mode, the second blue laser light is incident on the phosphor 44. Accordingly, white light having a spectrum shown in FIG. 3 (second white light) is emitted to the inside of the subject. The second white light is configured to include second blue laser light and second fluorescence of green to red that is excited and emitted from the phosphor 44 by the second blue laser light. Accordingly, the wavelength range of the second white light is the entire visible light region.

Figure 4:
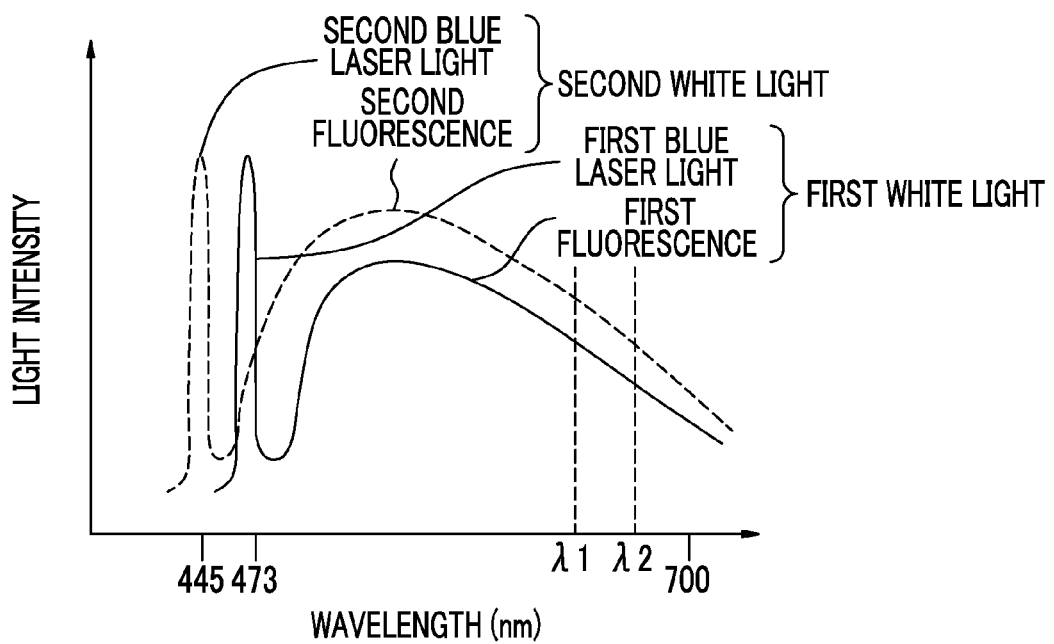
FIG. 4 is a graph showing the spectra of first white light and second white light emitted in a special observation mode.

On the other hand, in the special observation mode, the first blue laser light and the second blue laser light are alternately incident on the phosphor 44. Therefore, first white light and second white light having the spectrums shown in FIG. 4 are alternately emitted to the inside of the subject. The first white light is configured to include first blue laser light and first fluorescence of green to red that is excited and emitted from the phosphor 44 by the first blue laser light. Accordingly, the wavelength range of the first white light is the entire visible light region. The second white light is the same as the second white light emitted in the normal observation mode.

The first fluorescence and the second fluorescence have almost the same waveform (shape of the spectrum), and the ratio between the intensity ($I1(\lambda)$) of the first fluorescence and the intensity ($I2(\lambda)$) of the second fluorescence (hereinafter, referred to as an inter-frame intensity ratio) is the same at any wavelength $\lambda$. For example, it is $I2(\lambda 1)/I1(\lambda 1) = I2(\lambda 2)/I1(\lambda 2)$. Since the inter-frame intensity ratio $I2(\lambda)/I1(\lambda)$ affects the calculation accuracy of the oxygen saturation, the inter-frame intensity ratio I2 (λ)/I1 (λ) is accurately controlled by the light source control unit 40 such that the inter-frame intensity ratio set in advance is maintained.

As the phosphor 44, it is preferable to use a phosphor that absorbs some of the first and second blue laser light beams and includes a plurality of kinds of phosphors (for example, a YAG-based phosphor or a phosphor, such as BAM ($BaMgAl_{10}O_{17}$)) that are excited to emit green to red light beams. If a semiconductor light emitting device is used as a light source for exciting the phosphor 44 as in the present embodiment, it is possible to obtain high-intensity first and second white light beams with high luminous efficiency. In addition, it is possible to easily adjust the intensity of the white light and to suppress changes in color temperature and chromaticity.

The imaging optical system 24b of the endoscope 12 includes an imaging lens 46, the zoom lens 47, and an image sensor 48 (refer to FIG. 2). Reflected light from the subject is incident on the image sensor 48 through the imaging lens 46 and the zoom lens 47. Therefore, a reflected image of the subject is formed on the image sensor 48. The zoom lens 47 is moved between the tele end and the wide end by operating the zoom operation unit 22c. When the zoom lens 47 is moved to the wide end side, the reflected image of the subject is reduced. On the other hand, when the zoom lens 47 is moved to the tele end side, the reflected image of the subject is magnified. In addition, in a case in which magnified observation is not performed (at the time of non-magnified observation), the zoom lens 47 is disposed at the wide end. In the case of performing magnified observation, the zoom lens 47 is moved from the wide end to the tele end side by operating the zoom operation unit 22c.

The image sensor 48 is a color imaging device, and captures a reflected image of the subject by receiving the reflected light, which is reflected from the subject, and outputs the image signal. For example, the image sensor 48 is a charge coupled device (CCD) image sensor or a complementary metal-oxide semiconductor (CMOS) image sensor. In addition, the image sensor 48 includes RGB pixels in which RGB color filters are provided on the imaging surface, and outputs image signals of three colors of R, and B by performing photoelectric conversion in the pixels of respective colors of RGB.

Figure 5:
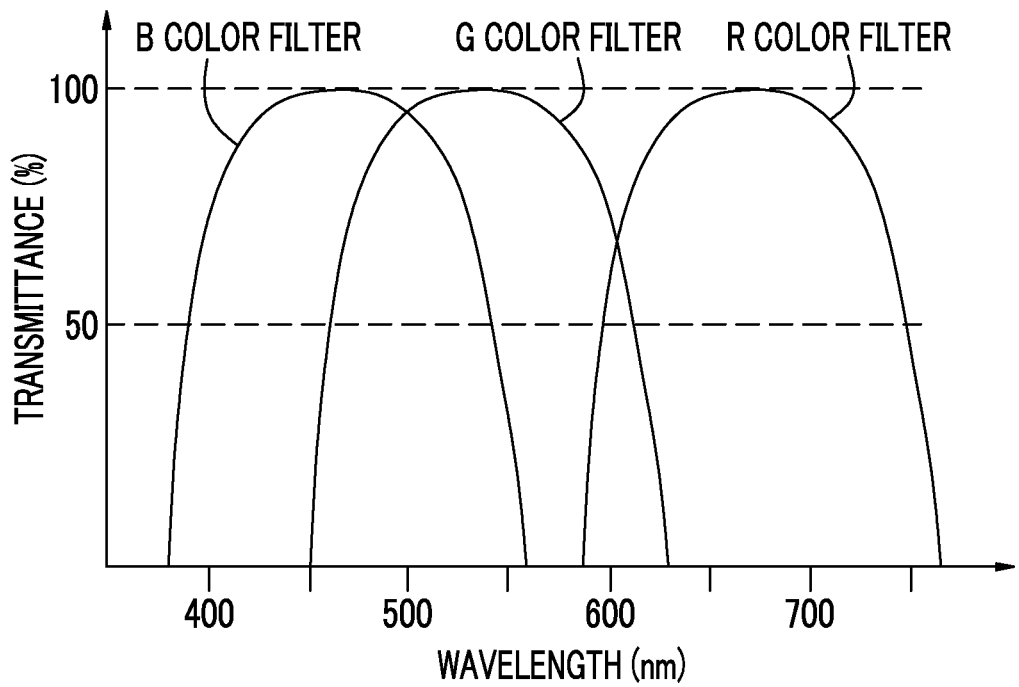
FIG. 5 is a graph showing the spectral transmittance of an RGB color filter.

As shown in FIG. 5, the B color filter has a spectral transmittance of 380 nm to 560 nm, the G color filter has a spectral transmittance of 450 nm to 630 nm, and the R color filter has a spectral transmittance of 580 nm to 760 nm. Accordingly, in a case in which the second white light is emitted to the inside of the subject in the normal observation mode, the second blue laser light and some of green components of the second fluorescence are incident on the B pixel, some of green components of the second fluorescence are incident on the G pixel, and red components of the second fluorescence are incident on the R pixel. However, since the emission intensity of the second blue laser light is extremely larger than that of the second fluorescence, most of the B image signal output from the B pixel is occupied by the reflected light components of the second blue laser light.

On the other hand, in a case in which the first white light is emitted to the inside of the subject in the special observation mode, the first blue laser light and some of green components of the first fluorescence are incident on the B pixel, some of green components of the first fluorescence are incident on the G pixel, and red components of the first fluorescence are incident on the R pixel. However, since the emission intensity of the first blue laser light is extremely larger than that of the first fluorescence, most of the B image signal is occupied by the reflected light components of the first blue laser light. Light incidence components in the respective RGB pixels when the second white light is emitted to the inside of the subject in the special observation mode are the same as those in the normal observation mode.

As the image sensor 48, it is also possible to use a so-called complementary color image sensor including complementary color filters of cyan (C), magenta (M), yellow (Y), and green (G) on the imaging surface. In the case of using the complementary color image sensor as the image sensor 48, a color converter that performs color conversion from image signals of four colors of CMYG to image signals of three colors of RGB is preferably provided in the endoscope 12, the light source device 14, or the processor device 16. In this manner, even in a case in which complementary color image sensors are used, it is possible to obtain the image signals of three colors of RGB from the image signals of four colors of CMYG by color conversion.

Figure 6:
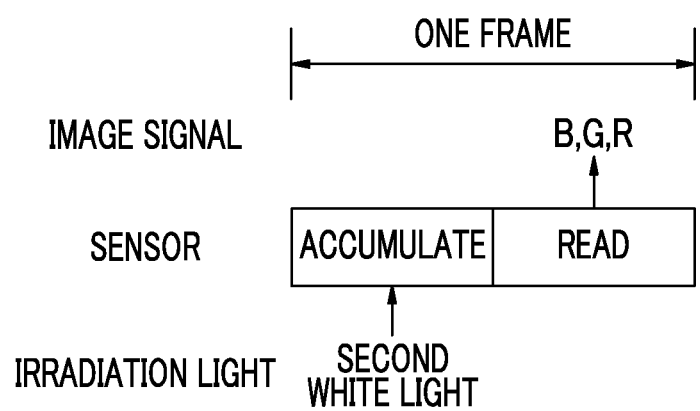
FIG. 6 is an explanatory diagram showing imaging control in the normal observation mode.

An imaging control unit 49 controls the imaging of the image sensor 48. As shown in FIG. 6, the period of one frame of the image sensor 48 includes an accumulation period, for which electric charges are accumulated by photoelectrically converting the reflected light from the subject, and a readout period subsequent thereto, for which an image signal is output by reading the accumulated electric charges. In the normal observation mode, the inside of the subject illuminated with the second white light is imaged by the image sensor 48 for each period of one frame. Then, the image signals of RGB are output from the image sensor 48 for each frame.

Figure 7:
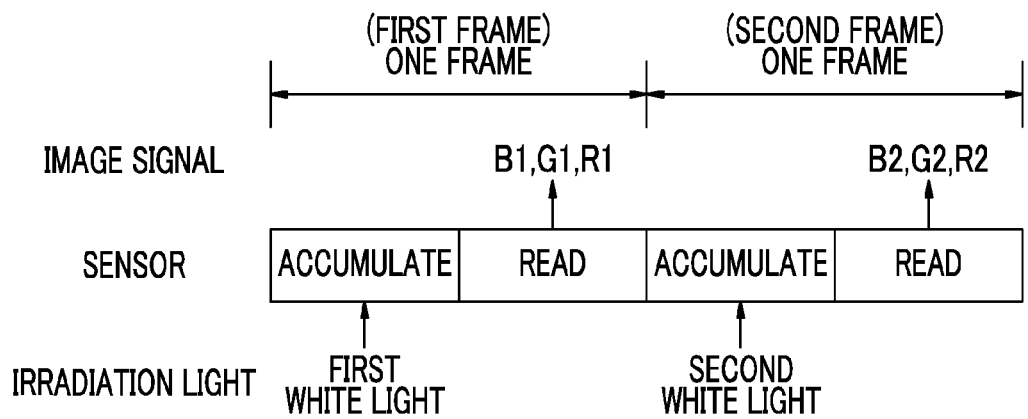
FIG. 7 is an explanatory diagram showing imaging control in the special observation mode.

Also in the special observation mode, the imaging control unit 49 causes the image sensor 48 to accumulate electric charges and output an image signal in the same manner as in the normal observation mode. However, in the special observation mode, the first white light and the second white light are alternately emitted to the inside of the subject in synchronization with the imaging frame of the image sensor 48. Therefore, as shown in FIG. 7, the image sensor 48 images the inside of the subject illuminated with the first white light in the first frame, and images the inside of the subject illuminated with the second white light in the next second frame. The image sensor 48 outputs the image signals of RGB colors in both the first and second frames. However, the spectrum of white light in the first frame and the spectrum of white light in the second frame are different. Therefore, for the sake of distinction, the image signals of RGB colors obtained by imaging the subject illuminated with the first white light in the first frame are referred to as an R1 image signal, a G1 image signal, and a B1 image signal, and the image signals of RGB colors obtained by imaging the subject illuminated with the second white light in the second frame are referred to as an R2 image signal, a G2 image signal, and a B2 image signal.

In order to calculate the oxygen saturation, a signal ratio B1/G2 between the B1 image signal and the G2 image signal and a signal ratio R2/G2 between the R2 image signal and the G2 image signal are used. Between these signal ratios, the signal ratio B1/G2 between the B1 image signal and the G2 image signal is an essential signal ratio for the calculation of oxygen saturation. In the present embodiment, therefore, a component (first blue laser light transmitted through the phosphor 44) that becomes the B1 image signal in the first white light is the first signal light, and a component (green band component of the second fluorescence) that becomes the G2 image signal in the second white light is the second signal light.

The image signals of the respective colors output from the image sensor 48 are transmitted to a correlated double sampling (CDS)/automatic gain control (AGC) circuit 50 (refer to FIG. 2). The CDS/AGC circuit 50 performs correlated double sampling (CDS) or automatic gain control (AGC) for the analog image signals output from the image sensor 48. The image signals transmitted through the CDS/AGC circuit 50 are converted into digital image signals by an A/D converter 52. The image signals that have been digitized in this manner are input to the processor device 16.

The processor device 16 includes a receiving unit 54, an image processing switching unit 60, a normal observation image processing unit 62, an observation distance measurement unit 63, a special observation image processing unit 64, and an image display signal generation unit 66. The receiving unit 54 receives the image signal input from the endoscope 12. The receiving unit 54 includes a digital signal processor (DSP) 56 and a noise removal section 58, and the DSP 56 performs digital signal processing, such as color correction processing, on the received image signal. The noise removal section 58 performs noise removal processing using, for example, a moving average method or a median filter method, on the image signal obtained after the color correction processing or the like in the DSP 56. The image signals after noise has been removed are input to the image processing switching unit 60.

in a case in which the mode selector SW 22b is set to the normal observation mode, the image processing switching unit 60 inputs the image signals to the normal observation image processing unit 62. On the other hand, in a case in which the mode selector SW 22b is set to the special observation mode, the image processing switching unit 60 inputs the image signals to the observation distance measurement unit 63 and the special observation image processing unit 64.

The normal observation image processing unit 62 includes a color conversion section 68, a color enhancement section 70, and a structure enhancement section 72. The color conversion section 68 generates RGB image data by assigning the input RGB image signals of one frame to R, and B pixels. Then, color conversion processing, such as 3×3 matrix processing, gradation conversion processing, and three-dimensional LUT processing, is performed on the RGB image data.

The color enhancement section 70 performs various kinds of color enhancement processing on the RGB image data after the color conversion processing. The structure enhancement section 72 performs structure enhancement processing, such as spatial frequency enhancement, on the RGB image data after the color enhancement processing. The RGB image data subjected to the structure enhancement processing by the structure enhancement section 72 is input to the image display signal generation unit 66 as a normal observation image.

The observation distance measurement unit 63 measures a distance (observation distance) between the subject and the distal portion 24 based on the image signal. The observation distance calculated by the observation distance measurement unit 63 is input to the special observation image processing unit 64 (oxygen saturation image generation section 76). In the case of performing magnified observation by driving the zoom lens 47, the distance between the distal portion 24 and the subject is not changed. However, the subject is observed so as to be magnified in the same manner as in a case in which the distal portion 24 is brought close to the subject. For this reason, the magnified observation when the zoom lens 47 is driven has substantially the same function as bringing the distal portion 24 close to the subject. Therefore, a substantial observation distance based on the zoom magnification at the time of magnified observation when the zoom lens 47 is driven is included in the observation distance measured by the observation distance measurement unit 63.

The special observation image processing unit 64 includes an oxygen saturation image generation section 76 and a structure enhancement section 78. The oxygen saturation image generation section 76 calculates oxygen saturation, and generates an oxygen saturation image indicating the calculated oxygen saturation. In addition, the oxygen saturation image generation section 76 calculates oxygen saturation that has been corrected according to the observation distance. Therefore, the oxygen saturation calculated by the oxygen saturation image generation section 76 is a highly accurate value even in a case in which the observation distance is changed.

The structure enhancement section 78 performs structure enhancement processing, such as spatial frequency enhancement processing, on the oxygen saturation image input from the oxygen saturation image generation section 76. The oxygen saturation image subjected to the structure enhancement processing by the structure enhancement section 72 is input to the image display signal generation unit 66.

The image display signal generation unit 66 converts the normal observation image or the oxygen saturation image into a display format signal (display image signal), and inputs the display format signal to the monitor 18. As a result, the normal observation image or the oxygen saturation image is displayed on the monitor 18.

Figure 8:
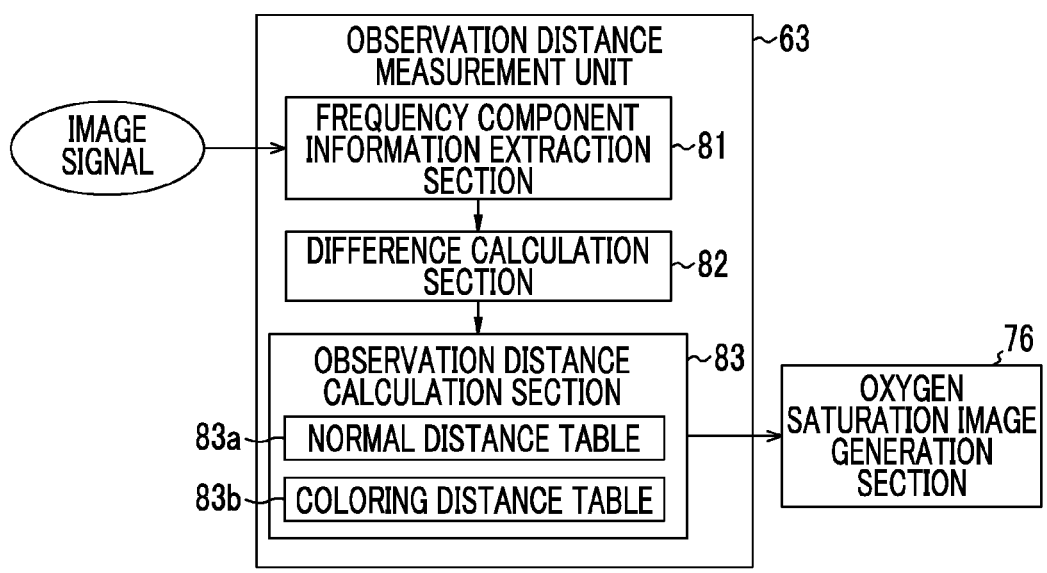
FIG. 8 is a block diagram of an observation distance measurement unit.

As shown in FIG. 8, the observation distance measurement unit 63 includes a frequency component information extraction section 81, a difference calculation section 82, and an observation distance calculation section 83.

The frequency information extraction section 81 acquires a B1 image signal, a G2 image signal, and an R2 image signal, which are used in the calculation of oxygen saturation, and extracts frequency component information. Specifically, a Fourier transform of each of the acquired image signals is performed to calculate the amplitude P(B1), P(G2), and P(R2), and the amplitude of a specific frequency component is extracted from each of the amplitudes P(B1), P(G2), and P(R2). For example, the specific frequency component is a frequency component corresponding to superficial blood vessels, a ductal structure, or the like that is a main observation target in the case of performing observation in a short-distance view with a short observation distance by bringing the distal portion 24 close to the subject.

The difference calculation section 82 calculates a difference of the specific frequency component between the amplitudes P(B1), P(G2), and P(R2) extracted by the frequency component information extraction section 81. That is, a difference $\Delta BG$ (=P(B1)−P(G2)) between the amplitudes of specific frequency components of the B1 image signal and the G2 image signal, a difference $\Delta GR$ (=P(G2)−P(R2)) between the amplitudes of specific frequency components of the G2 image signal and the R2 image signal, and a difference $\Delta RB$ (=P(R2)−P(B1)) between the amplitudes of specific frequency components of the R2 image signal and the B1 image signal are calculated for each specific frequency component.

Figure 9:
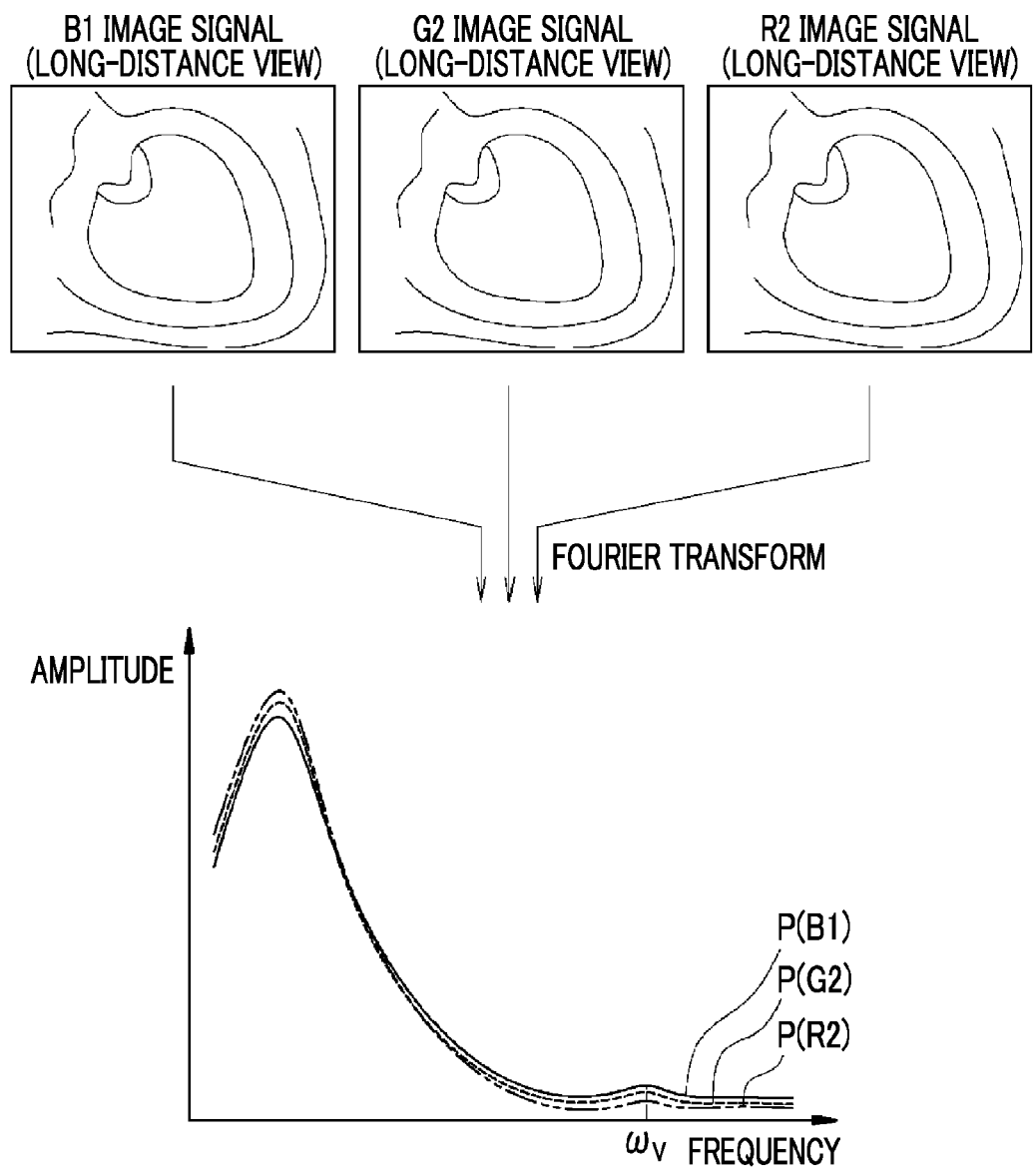
FIG. 9 is an explanatory diagram showing image signals in a long-distance view and the amplitudes of frequency components.

For example, as shown in FIG. 9, in a B1 image signal (long-distance view), a G2 image signal (long-distance view), and an R2 image signal (long-distance view) that are obtained in the case of observation in a long-distance view with a long observation distance, a fine image, such as superficial blood vessels, cannot be observed. For this reason, there is almost no difference among the amplitude differences ΔBG, ΔGR, and ΔRB at a specific frequency $\omega_v$ corresponding to the superficial blood vessels or the like. In FIG. 9, amplitudes according to the Fourier transform along an arbitrary direction are expressed for convenience. However, the Fourier transform performed by the frequency component information extraction section 81 is a two-dimensional Fourier transform. The frequency component information extraction section 81 extracts an amplitude value at the specific frequency $\omega_v$. The amplitude differences ΔBG, ΔGR, and ΔRB calculated by the difference calculation section 82 are differences between the peak values of the amplitudes P(B1), P(G2), and P(R2) at the specific frequency $\omega_v$.

Figure 10:
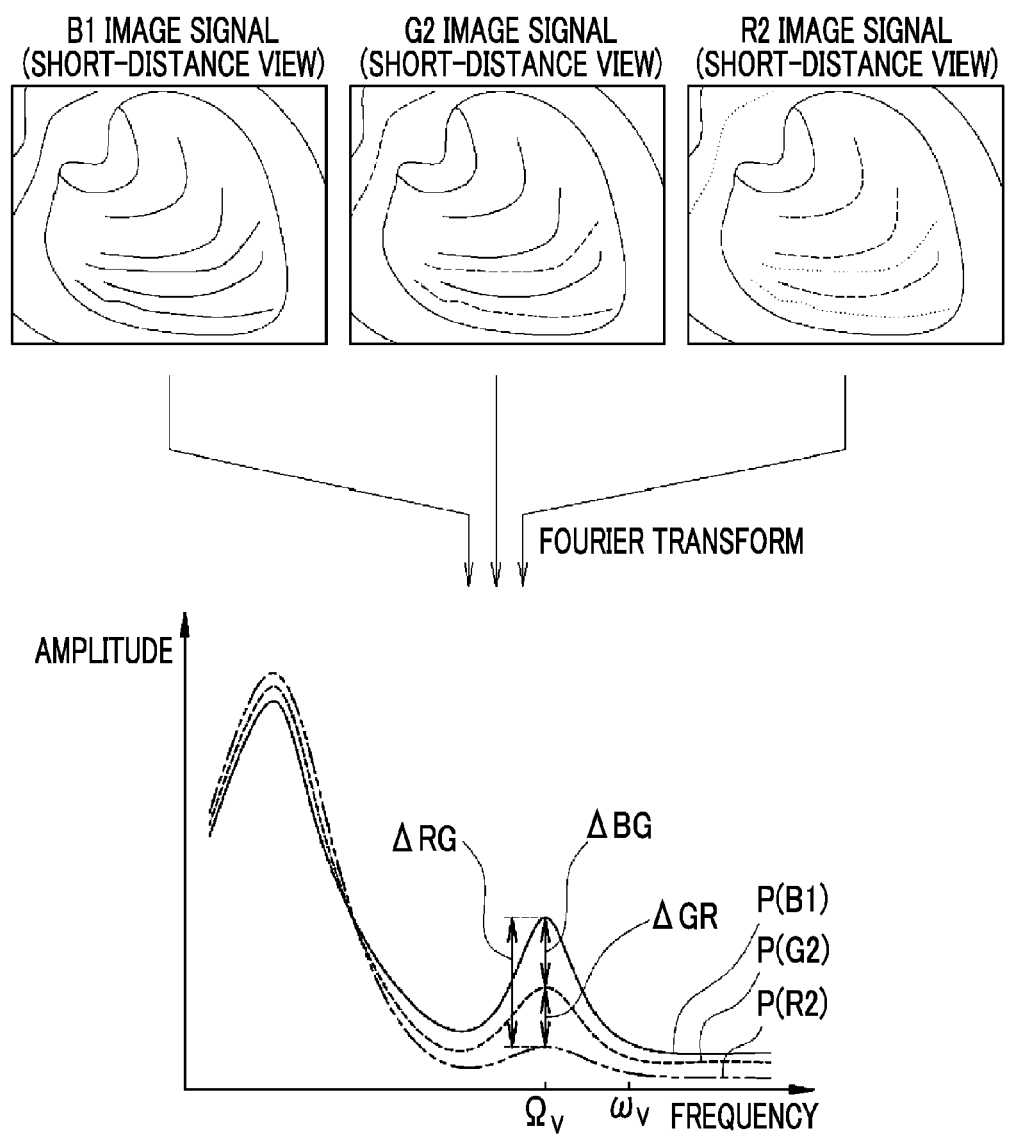
FIG. 10 is an explanatory diagram showing image signals in a short-distance view and the amplitudes of frequency components.

On the other hand, as shown in FIG. 10, a fine image, such as superficial blood vessels, appears in a B1 image signal (short-distance view) obtained by bringing the distal portion 24 close to the subject (or by performing magnified observation using the zoom lens 47). However, an image appearing in the G2 image signal (short-distance view) is blurred rather than the B1 image signal (short-distance view). In addition, an image appearing in the R2 image signal (short-distance view) is blurred rather than the G2 image signal (short-distance view). The difference in the blurriness of the image appearing in the image signal of each color is because the degree of penetration of light into the subject or the absorption of light into the subject (in particular, absorption of hemoglobin), scattering, and the like differ depending on each wavelength band. For this reason, at the specific frequency $\Omega_v$ corresponding to the superficial blood vessels or the like in a case in which the observation distance is short (in the case of a short-distance view), a noticeable difference occurs between the amplitudes P(B1), P(G2), and P(R2), and a difference also occurs between the amplitude differences ΔBG, ΔGR, and ΔRB. Accordingly, the amplitude differences ΔBG, ΔGR, and ΔRB indicate the balance of the blurriness of the image between the respective colors.

In addition, as the observation distance becomes shorter, the superficial blood vessels or the like are viewed thicker (larger). Accordingly, the specific frequency $\Omega_v$ corresponding to the superficial blood vessels or the like is shifted to the low frequency side from the frequency $\omega_v$ at the time of long-distance view. Since the amplitudes P(B1), P(G2), and P(R2) at the time of magnified observation are shifted approximately to the low frequency side in general compared with those in the case of a long-distance view in which the observation distance is long, the correspondence relationship between the specific frequency $\omega_v$ in a case in which the observation distance is short and the specific frequency $\Omega_v$ at the time of magnified observation can be easily detected from the overall waveforms of the amplitudes P(B1), P(G2), and P(R2).

In a case in which the observation distance is fixed, the blurriness of the image corresponding to the wavelength is also almost fixed. Accordingly, each of the amplitude differences ΔBG, ΔGR, and ΔRB also becomes a specific value corresponding to the zoom magnification or the distance between the distal portion 24 and the subject. By using this fact, the observation distance calculation section 83 calculates the observation distance based on the amplitude differences ΔBG, ΔGR, and ΔRB.

However, in a case in which a colorant is introduced (sprayed or administered) into the subject in order to facilitate the observation of a specific tissue, the balance of the amplitude of the specific frequency $\Omega_v$ is lost due to the presence of the colorant, and the balance of the amplitude differences ΔBG, ΔGR, and ΔRB is also lost.

In the inspection using an endoscope, for example, indigo carmine may be sprayed to the inside of the subject as a colorant (dye solution). Indigo carmine is a dark blue colorant having an absorption spectrum shown in FIG. 11. When indigo carmine is sprayed to the inside of the subject, the indigo carmine is collected in a ductal structure (pit pattern). Accordingly, since the ductal structure is colored in dark blue, the ductal structure is emphasized. In addition, irregularities of a lesion are easily observed by the pattern (distribution or density) of the emphasized ductal structure. On the other hand, since the indigo carmine is collected almost only in the ductal structure, the balance of the amplitudes of the image signals of the respective colors at the specific frequency $\Omega_v$ corresponding to this is lost. Specifically, the amplitude of the specific frequency $\Omega_v$ is increased in the B1 image signal, and the amplitude of the specific frequency $\Omega_v$ is reduced in the G2 image signal and the R2 image signal. Accordingly, the amplitude differences ΔBG, ΔGR, and ΔRB also change from specific values in a case in which the indigo carmine is not sprayed.

The indigo carmine is used in a so-called contrast method described above. However, other than the indigo carmine, toluidine blue or methylene blue is used in a staining method for staining a specific tissue so as to be emphasized. In a reaction method for emphasis observation based on reaction with a specific tissue, compound iodine glycerin (Lugol's solution) or crystal violet is used. In a fluorescence method for emphasis observation of a specific tissue using fluorescence, fluorescein or acridine orange is used. In an intravascular dye administration method for emphasizing the tissue by intravascular administration, for example, indocyanine green is used. In addition, there is also an emphasis method to whiten the superficial tissue of the subject by spraying acetic acid. in a case in which such various colorants or the like is introduced (sprayed or administered) into the subject, the balance of the image signals of the respective colors (in particular, the balance of the amplitude of the specific frequency $\Omega_v$) is changed compared with a case in which these are not introduced, as in the case in which the indigo carmine is sprayed. Needless to say, the way of change differs depending on the introduced colorant or the like.

For these reasons, the observation distance measurement unit 63 has switchable measurement modes for measuring two observation distances of first and second measurement modes. Corresponding to each measurement mode, the observation distance calculation section 83 has a normal distance table 83a and a coloring distance table 83b.

Figures 11, 12:
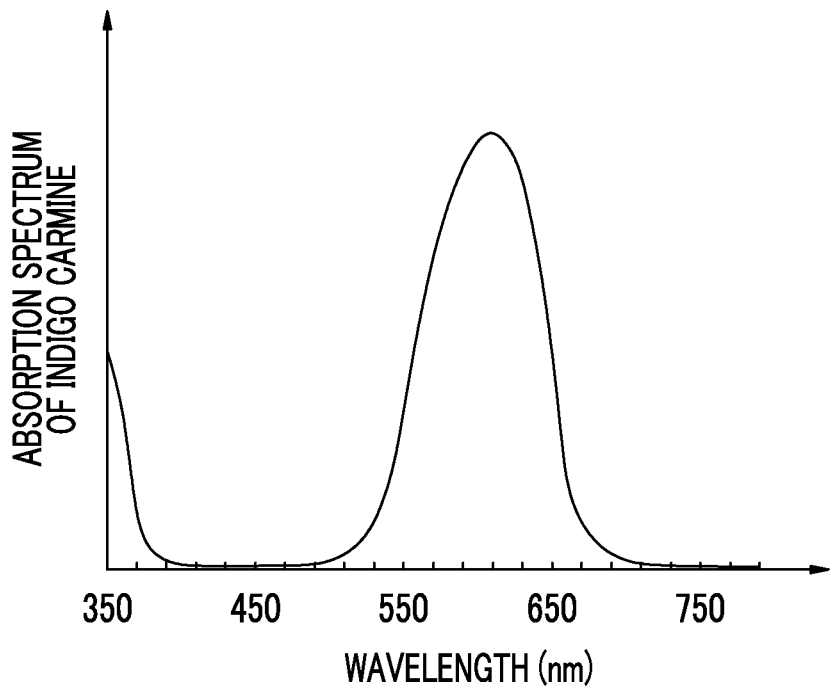
FIG. 11 is a graph showing the absorption spectrum of indigo carmine.
FIG. 12 is an explanatory diagram showing a normal distance table.

The first measurement mode is a mode for calculating the observation distance in the case of observing the subject with almost only the absorption characteristics of hemoglobin without a colorant or the like being introduced into the subject, that is, in the case of a normal observation environment. The normal distance table 83a is a table used in the first measurement mode, and is a table in which the amplitude differences ΔBG, ΔGR, and ΔRB at the time of normal observation are associated with the observation distance corresponding to the balance as shown in FIG. 12. The observation distance calculation section 83 calculates the observation distances corresponding to the amplitude differences ΔBG, ΔGR, and ΔRB, which are input from the difference calculation section 82, with reference to the normal distance table 83a at the time of normal observation.

Figures 13, 14:
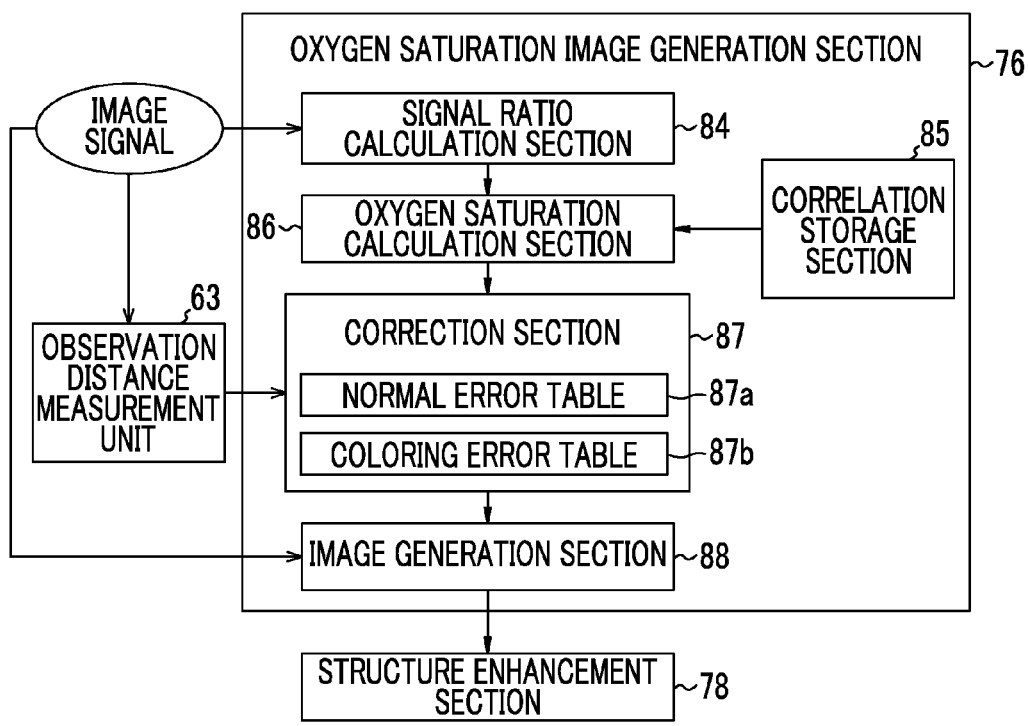
FIG. 13 is an explanatory diagram showing a coloring distance table.
FIG. 14 is a block diagram of an oxygen saturation image generation section.

The second measurement mode is a mode for calculating the observation distance in a case in which not only hemoglobin but also a substance (non-hemoglobin substance), such as a colorant having dominant absorption characteristics that changes the balance of the image signals of the respective colors, is present in the subject and the balance of the image signals of the respective colors and the amplitude of the specific frequency is changed by the absorption characteristics of the introduced colorant or the like (hereinafter, referred to as "at the time of coloring). The coloring distance table 83b is a table used in the second measurement mode, and is a table in which the amplitude differences ΔBG, ΔGR, and ΔRB at the time of coloring are associated with the observation distance corresponding to the balance as shown in FIG. 13. In a case in which the subject is colored with a colorant or the like, the observation distance calculation section 83 calculates the observation distances corresponding to the amplitude differences ΔBG, ΔGR, and ΔRB, which are input from the difference calculation section 82, with reference to the coloring distance table 83b.

When the normal distance table 83a is compared with the coloring distance table 83b, for example, even if the observation distance is the same, the corresponding amplitude differences ΔBG, ΔGR, and ΔRB are different depending on the presence of a colorant. On the contrary, even if the values (balances) of the amplitude differences ΔBG, ΔGR, and ΔRB are the same values, the corresponding observation distance differs depending on the presence of a colorant.

As shown in FIG. 14, the oxygen saturation image generation section 76 includes a signal ratio calculation section 84, a correlation storage section 85, an oxygen saturation calculation section 86, a correction section 87, and an image generation section 88.

Among the image signals of two frames that are input to the oxygen saturation image generation section 76, the B1 image signal, the G2 image signal, and the R2 image signal are input to the signal ratio calculation section 84. The signal ratio calculation section 84 calculates the signal ratios B1/G2 between the B1 image signal and the G2 image signal and the signal ratio R2/G2 between the G2 image signal and the R2 image signal for each pixel.

Figure 15:
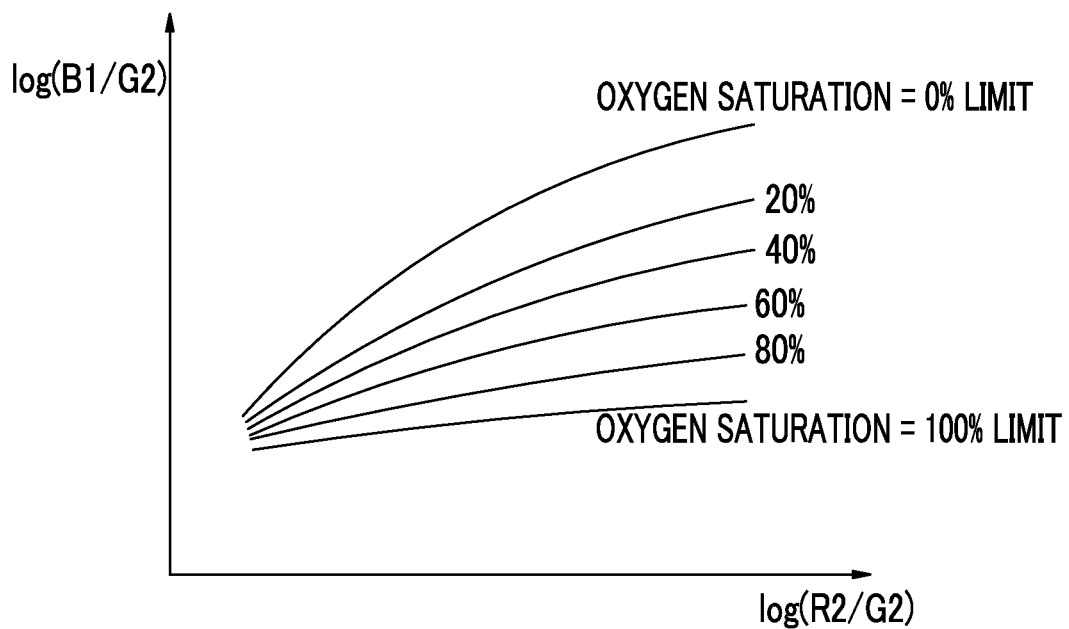
FIG. 15 is a graph showing the correlation between the signal ratios B1/G2 and R2/G2 and the oxygen saturation.

The correlation storage section 85 stores the correlation between the signal ratios B1/G2 and R2/G2 and the oxygen saturation. This correlation is stored in a two-dimensional table that defines the isolines of the oxygen saturation on the two-dimensional space shown in FIG. 15. The position and shape of the isolines for the signal ratios B1/G2 and R2/G2 are obtained in advance by physical simulation of light scattering, and the distance between the isolines changes according to the blood volume (signal ratio R2/G2). In addition, the correlation between the signal ratios B1/G2 and R2/G2 and the oxygen saturation is stored in a log scale.

Figure 16:
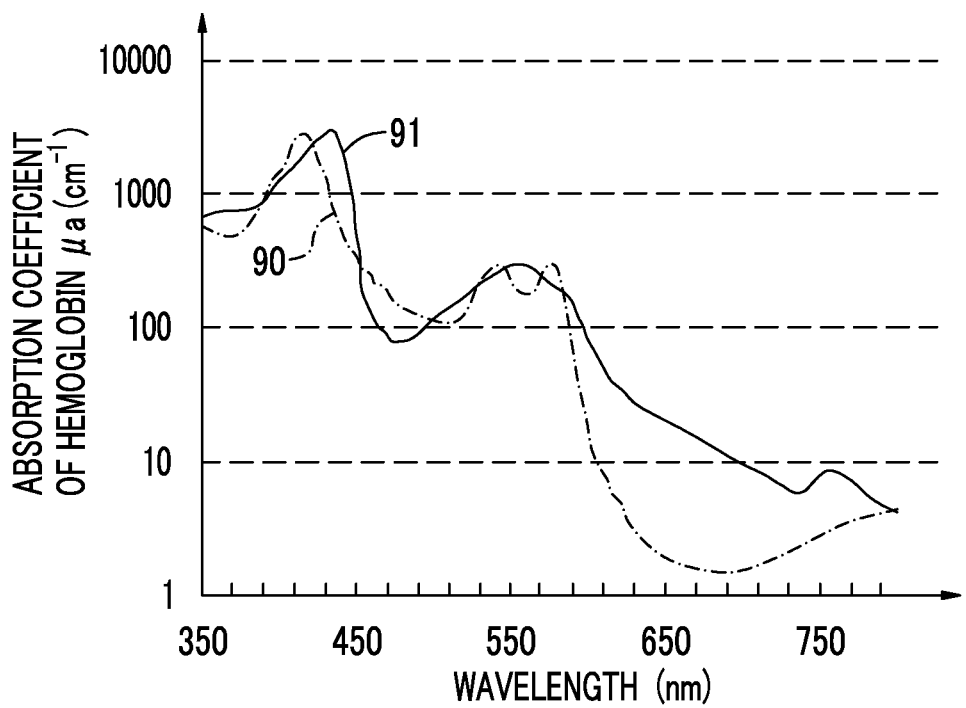
FIG. 16 is a graph showing the absorption coefficients of oxygenated hemoglobin and reduced hemoglobin.

As shown in FIG. 16, this correlation is closely related to the absorption characteristics or light scattering characteristics of oxygenated hemoglobin (graph 90) or reduced hemoglobin (graph 91). For example, as at a center wavelength of 473 nm of the first blue laser light, at a wavelength at which the difference between the absorption coefficient of oxygenated hemoglobin and the absorption coefficient of reduced hemoglobin is large, it is easy to handle the information of the oxygen saturation. However, the B1 image signal including a signal corresponding to 473-nm light has a high dependence not only on the oxygen saturation but also on the blood volume. Therefore, by using not only the B1 image signal but also the signal ratios B1/G2 and R2/G2 obtained from the R2 image signal, which corresponds to light that changes mainly depending on the blood volume, and the G2 image signal, which is a reference signal of the B1 image signal and the R2 image signal, it is possible to accurately calculate the oxygen saturation without there being dependency on the blood volume.

Figures 17, 18:
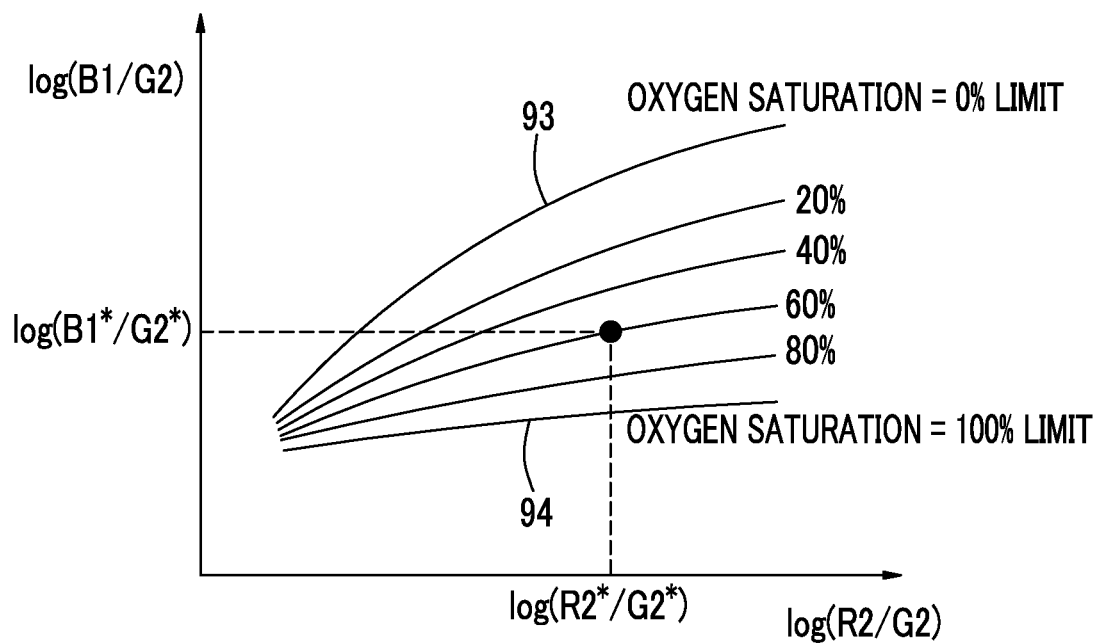
FIG. 17 is an explanatory diagram showing a method of calculating the oxygen saturation.
FIG. 18 is an explanatory diagram of a normal error table.

The oxygen saturation calculation section 86 calculates an oxygen saturation corresponding to the signal ratio B1/G2 and the signal ratio R2/G2 calculated by the signal ratio calculation section 84, for each pixel, with reference to the correlation stored in the correlation storage section 85. For example, in a case in which the signal ratio B1/G2 and the signal ratio R2/G2 in a specific pixel are B1*/G2* and R2*/G2*, respectively, the oxygen saturation corresponding to the signal ratio B1*/G2* and the signal ratio R2*/G2* is "60%" when the correlation shown in FIG. 17 is referred to. Accordingly, the oxygen saturation calculation section 86 calculates the oxygen saturation of the pixel as "60%". Thus, the oxygen saturation calculation section 86 calculates the oxygen saturation of the subject for each pixel based on the signal ratio between the image signals output from the same pixel.

In addition, a case in which the signal ratio B1/G2 and the signal ratio R2/G2 become extremely large or extremely small hardly occurs. That is, a case hardly occurs in which the value of the signal ratio B1/G2 or the signal ratio R2/G2 exceeds the lower limit line 93 of the oxygen saturation of 0% or on the contrary becomes lower than the upper limit line 94 of the oxygen saturation of 100%. Here, the oxygen saturation calculation section 86 sets the oxygen saturation to 0% in a case in which the calculated oxygen saturation is lower than the lower limit line 93, and sets the oxygen saturation to 100% in a case in which the calculated oxygen saturation exceeds the upper limit line 94. In addition, in a case in which a point corresponding to the signal ratio B1/G2 and the signal ratio R2/G2 deviates from a region between the lower limit line 93 and the upper limit line 94, display showing that the reliability of the oxygen saturation in the pixel is low may be performed, or the oxygen saturation may not be calculated.

The observation distance measured (calculated) by the observation distance measurement unit 63 is input to the correction section 87, and the correction section 87 corrects the error of the oxygen saturation calculated by the oxygen saturation calculation section 86 according to the input observation distance. The correction section 87 has a normal error table 87a and a coloring error table 87b corresponding to the first and second measurement modes of the observation distance measurement unit 63, and corrects the error of the oxygen saturation using the error tables 87a and 87b.

As shown in FIG. 18, the normal error table 87a is data in which an observation distance in a case in which a colorant or the like is not introduced into the subject is associated with the error of the oxygen saturation calculated under the observation distance. First, the correction section 87 calculates the error of the oxygen saturation corresponding to the amplitude differences ΔBG, ΔGR, and ΔRB, which are acquired from the difference calculation section 82, by referring to the normal error table 87a. Then, correction processing for eliminating the error is performed on the data of the oxygen saturation calculated by the oxygen saturation calculation section 86. For example, in a pixel in which the error is +10%, the error is subtracted (−10%) from the value of the corresponding oxygen saturation. In a case in which there is a variation in the correspondence relationship between the error of the oxygen saturation and the amplitude differences ΔBG, ΔGR, and ΔRB stored in the normal error table 87a, correction processing of the oxygen saturation is performed by estimating the most likely error of the oxygen saturation using a maximum likelihood method or the like.

At the time of normal observation when a colorant or the like is not introduced into the subject, an error may occur in oxygen saturation due to increasing the zoom magnification according to the degree in which the first white light or the second white light is not regarded as being uniformly emitted to the subject or due to bringing the distal portion 24 extremely close to the subject. The calculation of oxygen saturation is based on the assumption that the first white light or the second white light is uniformly emitted. Accordingly, when the non-uniformity of the first white light or the second white light is conspicuous, the balance of the B1 image signal, the G2 image signal, and the R2 image signal is lost accordingly. As a result, in the calculated oxygen saturation, error (hereinafter, referred to as artifacts) due to non-uniformity of the first white light or the second white light generated in a case in which the observation distance is too short occurs. The correction processing at the time of normal observation that the correction section 87 performs using the normal error table 87a is correction processing for correcting the artifacts.

Figure 19:
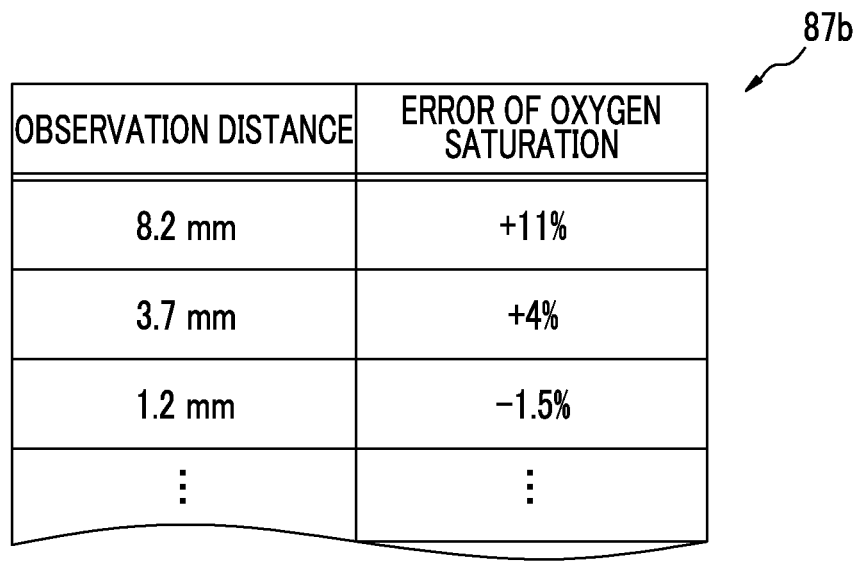
FIG. 19 is an explanatory diagram of a coloring error table.

As shown in FIG. 19, the coloring error table 87b is data in which an observation distance in a case in which a colorant or the like is introduced into the subject is associated with the error of the oxygen saturation calculated under the observation distance. Although the error of the oxygen saturation for the same observation distance is stored in the normal error table 87a and the coloring error table 87b, the error of the corresponding oxygen saturation differs depending on the presence of a colorant.

In a case in which the subject is colored, a specific tissue is observed in a different color from the color at the time of normal observation according to the introduced colorant. For this reason, in a portion of the colored tissue, the values of the signal ratio B1/G2 and the signal ratio R2/G2 for calculating the oxygen saturation become different values from the values at the time of normal observation. Accordingly, oxygen saturation is not calculated correctly. That is, an error due to the introduction of a colorant is included in the oxygen saturation. The correction processing that the correction section 87 performs using the coloring error table 87b is correction processing for correcting the error of the oxygen saturation due to the presence of a colorant in the subject as described above. In addition, artifacts appearing according to the observation distance in a case in which no colorant is present in the subject appear similarly even if a colorant is present in the subject if the same observation distance conditions are satisfied. According to the correction processing that the correction section 87 performs using the coloring error table 87b, such artifacts are also corrected simultaneously. Also in a case in which the coloring error table 87b is used, the method of correction processing by the correction section 87 is the same as in a case in which the normal error table 87a is used except that the used table is different.

The image generation section 88 generates an oxygen saturation image, which is obtained by imaging the oxygen saturation, using the oxygen saturation whose error has been corrected by the correction section 87 (hereinafter, referred to as a corrected oxygen saturation), the B2 image signal, the G2 image signal, and the R2 image signal. Specifically, the image generation section 88 applies a gain corresponding to the corrected oxygen saturation to the original B2 image signal, G2 image signal, and R2 image signal, which have been input, for each pixel, and generates RGB image data using the B2 image signal, the G2 image signal, and the R2 image signal after applying the gain. For example, in a pixel where the corrected oxygen saturation is 60% or more, the image generation section 88 multiplies all of the B2 image signal, the G2 image signal, and the R2 image signal by the same gain "1". In contrast, in a pixel where the corrected oxygen saturation is less than 60%, the image generation section 88 multiplies the B2 image signal by the gain less than "1" and multiplies the G2 image signal and the R2 image signal by the gain of "1" or more. RGB image data generated using the B2 image signal, the G2 image signal, and the R2 image signal after the gain processing is the oxygen saturation image.

In the oxygen saturation image generated by the image generation section 88, a high oxygen region (region having an oxygen saturation of 60% to 100%) is expressed in the same color as the normal observation image. On the other hand, a low oxygen region where the oxygen saturation is less than a specific value (region having an oxygen saturation of 0% to 60%) is expressed in a different color (pseudo-color) from the normal observation image.

Although the image generation section 88 performs gain multiplication for pseudo coloring only for the low oxygen region in the present embodiment, a gain corresponding to the oxygen saturation may also be multiplied for the high oxygen region so that the entire oxygen saturation image is pseudo-colored. In addition, although the low oxygen region and the high oxygen region are divided at the oxygen saturation of 60%, this boundary can be arbitrarily selected.

Figure 20:
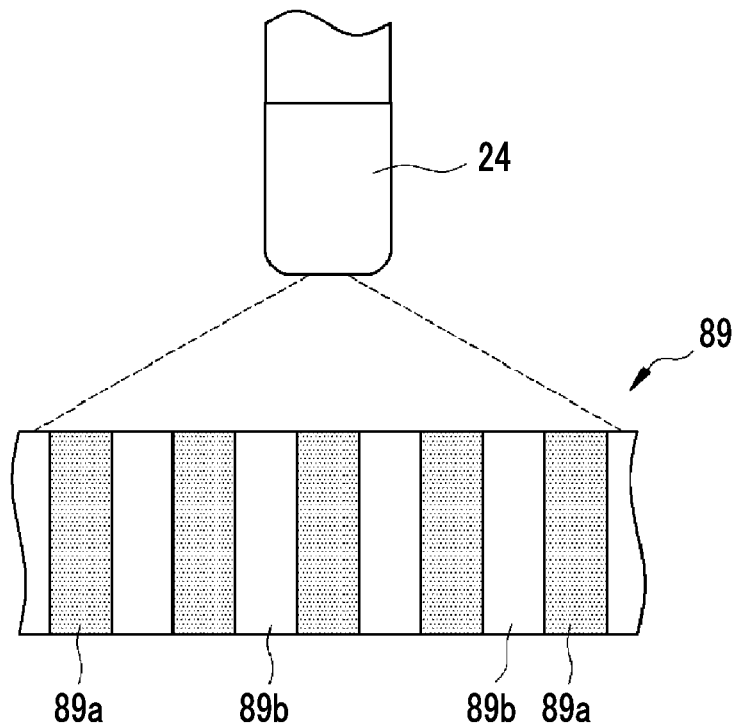
FIG. 20 is an explanatory diagram showing a phantom for generating a distance table or an error table.

The normal distance table 83a and the coloring distance table 83b stored in advance in the observation distance calculation section 83 and the normal error table 87a and the coloring error table 87b stored in advance in the correction section 87 are generated by measuring, for example, a phantom (simulation body formed by imitating a subject) 89 shown in FIG. 20 in the endoscope system 10. For example, the phantom 89 is formed by laminating gelatin containing the blood whose oxygen saturation is controlled to a specific value (hereinafter, referred to as blood-filled gelatin) 89a and gelatin containing no blood whose (hereinafter, referred to as bloodless gelatin) 89b at approximately the same specific spatial frequency as the superficial blood vessel of the subject. In a case in which there is no abnormality, such as a lesion, the oxygen saturation of the venous blood is generally 60% to 80%. Accordingly, the oxygen saturation of the blood-filled gelatin 89a is controlled to, for example, 70%.

The normal distance table 83a and the normal error table 87a are generated in the following procedures. First, the phantom 89 is observed while changing the zoom magnification or the distance from the distal portion 24, thereby calculating the oxygen saturation. The amplitude of the spatial frequency of the phantom 89 is extracted by performing a Fourier transform of the B1 image signal, the G2 image signal, and the R2 image signal, which are obtained by observing the phantom 89 by the frequency component information extraction section 81 and the difference calculation section 82, and the amplitude differences $\Delta BG$, $\Delta GR$, and $\Delta RB$ are calculated.

For example, in the case of observing the phantom 89 at a predetermined observation distance when the distal portion 24 is sufficiently away from the phantom 89 without zooming, the amplitude differences $\Delta BG$, $\Delta GR$, and $\Delta RB$ are approximately fixed values, and the error of the oxygen saturation is also approximately 0 (oxygen saturation 70%). On the other hand, when the observation distance is shortened by zooming or by bringing the distal portion 24 close to the phantom 89, there is a case in which the amplitude differences $\Delta BG$, $\Delta GR$, and $\Delta RB$ are larger (or smaller) than a specific value depending on the zoom magnification, the distance between the distal portion 24 and the phantom 89, or a combination thereof. In this case, since the calculated oxygen saturation becomes a larger value or conversely a smaller value than the oxygen saturation 70% of the blood-filled gelatin 89a, an error occurs.

By repeatedly performing such measurement while changing the observation distance, measurement data 96 in which the amplitude differences ΔBG, ΔGR, and ΔRB, the observation distance, and the error of the oxygen saturation are associated with each other as shown in FIG. 21 is obtained. In the measurement data 96, a table in which the amplitude differences ΔBG, ΔGR, and ΔRB and the corresponding observation distances are stored is the normal distance table 83a, and a table in which the observation distance and the corresponding error of the oxygen saturation are stored is the normal error table 87a.

The method of generating the coloring distance table 83b and the coloring error table 87b is the same as the method of generating the normal distance table 83a and the normal error table 87a, and the coloring distance table 83b and the coloring error table 87b are generated using the phantom 89. When generating the coloring distance table 83b and the coloring error table 87b, a colorant is sprayed (or injected) on the surface of the phantom 89 in the same manner as when introducing the colorant into the subject, and the amplitude differences ΔBG, ΔGR, and ΔRB, the observation distance, and the error of the oxygen saturation are measured while changing the observation distance. In the measurement data obtained by spraying the colorant, a table in which the amplitude differences ΔBG, ΔGR, and ΔRB and the corresponding observation distances are stored is the coloring distance table 83b, and a table in which the observation distance and the corresponding error of the oxygen saturation are stored is the coloring error table 87b.

Figure 22:
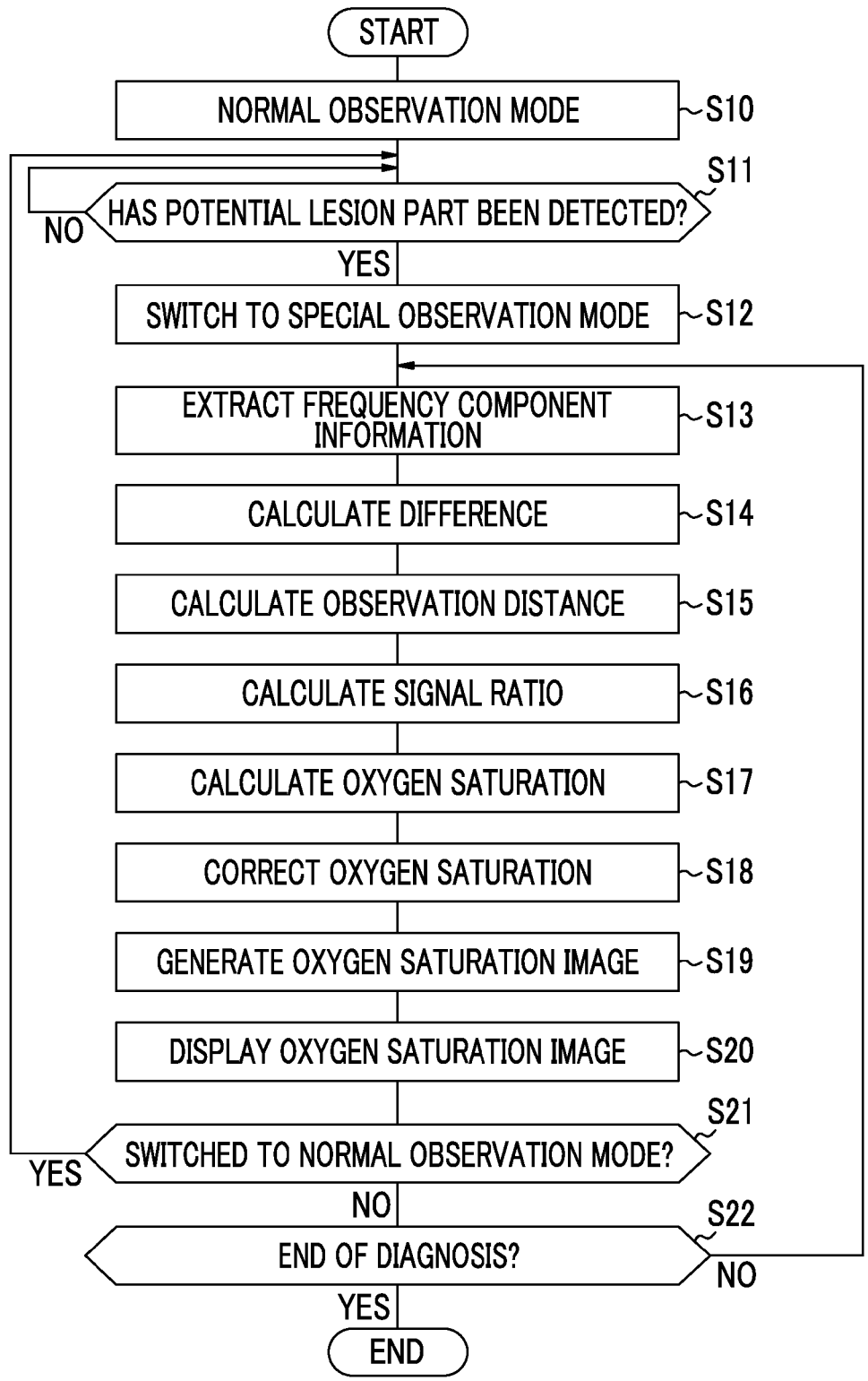
FIG. 22 is a flowchart showing the operation of the endoscope system.

Next, the flow of observation using the endoscope system 10 of the present embodiment will be described with reference to the flowchart in FIG. 22. First, in the normal observation mode, screening is performed from the most distant view state (S10). In the normal observation mode, a normal observation image is displayed on the monitor 18. In a case in which a part that is likely to be a lesion (hereinafter, referred to as a potential lesion part), such as a brownish area or rubor, is found in this screening (S11), the mode selector SW 22b is operated for switching to the special observation mode (S12). Then, in the special observation mode, it is determined whether or not the potential lesion part is in a low oxygen state.

In the special observation mode, the first and second white light beams are alternately emitted to the inside of the subject in synchronization with the imaging frame of the image sensor 48. Accordingly, the image sensor 48 outputs the R1 image signal, the G1 image signal, and the B1 image signal in a frame in which the first white light is emitted, and outputs the R2 image signal, the G2 image signal, and the B2 image signal in a frame in which the second white light is emitted.

Then, using the image signals of two frames, the observation distance measurement unit 63 measures an observation distance first. Specifically, the frequency component information extraction section 81 performs a Fourier transform of the B1 image signal, the G2 image signal, and the R2 image signal to extract the amplitude (frequency component information) of the specific frequency component corresponding to, for example, a superficial blood vessel (S13). Then, the differences ΔBG, ΔGR, and ΔRB between the amplitudes of the specific frequency components extracted from the image signals are calculated by the difference calculation section 82 (S14).

Then, the observation distance calculation section 83 calculates the observation distance based on the amplitude differences ΔBG, ΔGR, and ΔRB (S15). In the calculation of the observation distance, in a case in which the doctor has performed a setting indicating the introduction of a colorant using the processor device 16, the measurement mode of the observation distance measurement unit 63 is set to the second measurement mode, and the coloring distance table 83b is used in the observation distance calculation section 83. Otherwise, the measurement mode of the observation distance measurement unit 63 is set to the first measurement mode, and the normal distance table 83a is used in the observation distance calculation section 83. Therefore, an accurate observation distance is calculated regardless of the presence of a colorant in the subject.

On the other hand, the oxygen saturation image generation section 76 calculates the oxygen saturation, and generates an oxygen saturation image (S16 to S19). Specifically, the signal ratio calculation section 84 calculates the signal ratio B1/G2 and the signal ratio R2/G2 for each pixel (S16). Then, based on the signal ratio B1/G2 and the signal ratio R2/G2, the oxygen saturation calculation section 86 calculates the oxygen saturation for each pixel (S17).

Then, the correction section 87 calculates an error of the oxygen saturation corresponding to the observation distance calculated by the observation distance calculation section 83, and performs correction processing for eliminating the calculated error for the oxygen saturation calculated by the oxygen saturation calculation section 86, thereby calculating corrected oxygen saturation (S18). Since the method of correction processing is linked to the measurement mode of the observation distance measurement unit 63, the coloring error table 87b is used in a case in which the observation distance measurement unit 63 operates in the second measurement mode for coloring, and the normal error table 87a is used in a case in which the observation distance measurement unit 63 operates in the first measurement mode for normal observation. Therefore, accurate correction processing is performed regardless of the presence of a colorant in the subject.

After the corrected oxygen saturation is calculated by the correction section 87, the image generation section 88 generates an oxygen saturation image by multiplying each of the B2 image signal, the G2 image signal, and the R2 image signal by a gain corresponding to the corrected oxygen saturation (S19), and is displayed on the monitor 18 (S20). Based on the oxygen saturation image displayed on the monitor 18, the doctor checks whether or not the potential lesion part is in a low oxygen state.

Figure 23:
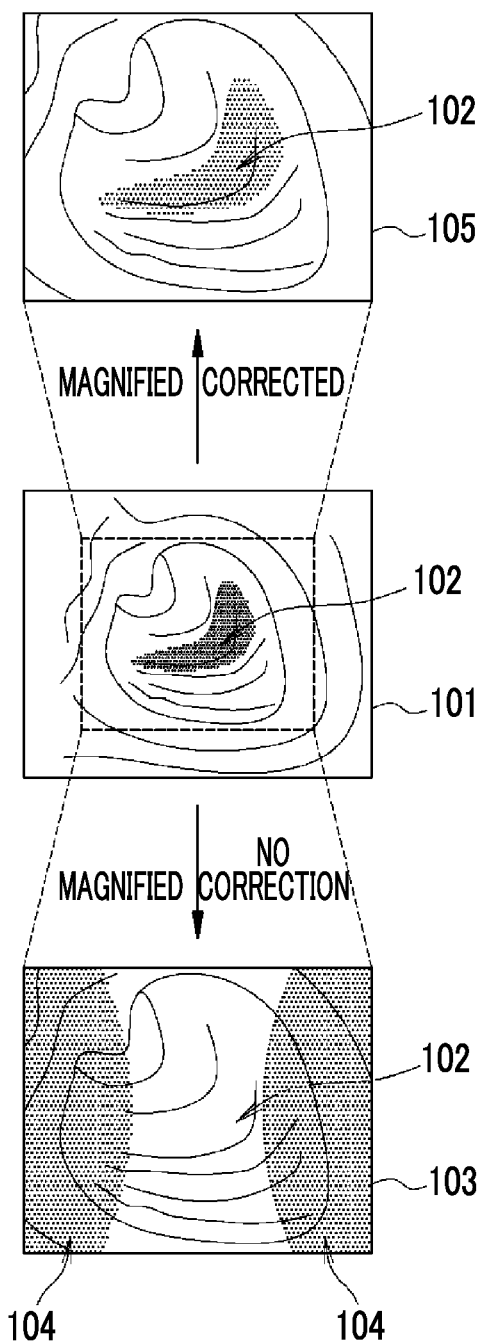
FIG. 23 is an explanatory diagram showing the effect of correction processing based on the observation distance at the time of normal observation.

For example, in the case of performing observation in a long-distance view without introducing a colorant into the subject, it is checked that the potential lesion part is a low oxygen region 102 in an oxygen saturation image 101 of a long-distance view, and the doctor brings the distal portion 24 close to the low oxygen region 102 (or performs a zooming operation) for magnified observation of the low oxygen region 102, as shown in FIG. 23. In this case, if the oxygen saturation correction processing of the correction section 87 is not performed, an artifact 104 appears in the calculated oxygen saturation as in an oxygen saturation image 103. As a result, a wrong (or incorrect) region due to magnification of the subject is displayed in pseudo-color showing a low oxygen state. In addition, when the artifacts of the high oxygen saturation overlap the original low oxygen region 102, even the low oxygen region 102 that has been observed at the time of observation in a long-distance view is hardly observed in some cases.

In the endoscope system 10, however, the oxygen saturation that the oxygen saturation calculation section 86 calculates on the assumption that the first white light or the second white light is uniform is not used as it is to generate an oxygen saturation image, but the oxygen saturation obtained after the correction section 87 performs correction processing according to the observation distance for the oxygen saturation calculated by the oxygen saturation calculation section 86 is used to generate an oxygen saturation image. For this reason, for example, as an oxygen saturation image 105, the low oxygen region 102 that has been observed in the long-distance view is enlarged and displayed as it is without errors. Therefore, in the endoscope system 10, it is possible to display the information of accurate oxygen saturation.

Figure 24:
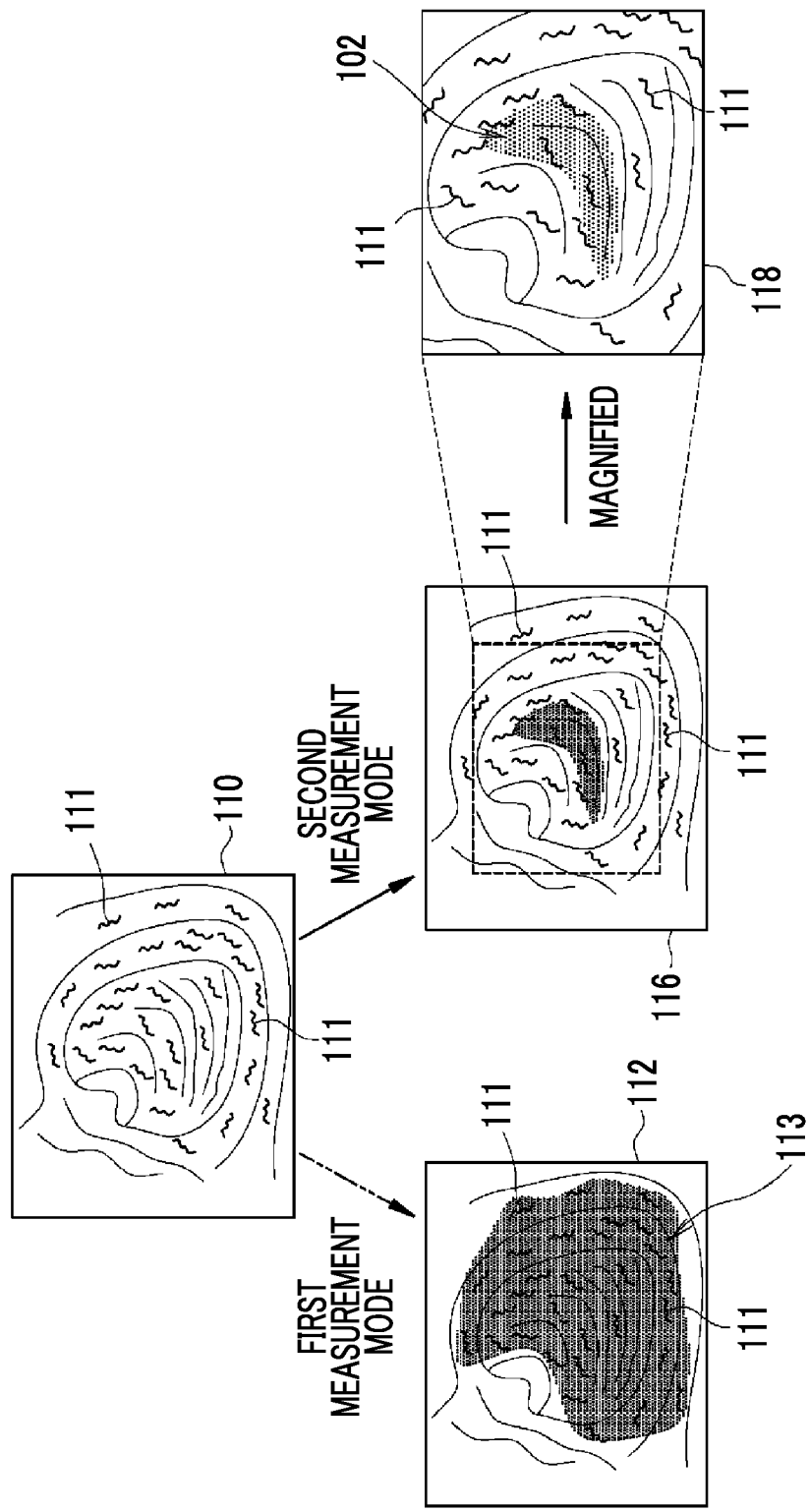
FIG. 24 is an explanatory diagram showing the effect of correction processing based on the observation distance at the time of coloring.

In addition, for example, in the case of observing the same position as the oxygen saturation image 101 by introducing a colorant into the subject, a normal observation image 110 in which a specific tissue 111 or the like is colored is displayed on the monitor 18 in the normal observation mode, as shown in FIG. 24. Then, it is assumed that switching to the special observation mode has occurred while maintaining the observation distance. In this case, when the observation distance is calculated in the first measurement mode for a case in which no colorant is present in the subject and the oxygen saturation is calculated and corrected, a wrong (or incorrect) part is displayed in pseudo-color as a low oxygen region 113 since the balance of the image signals of the respective colors is lost due to the specific tissue 111 being colored as an oxygen saturation image 112. This is the same for a case in which the observation distance is not calculated and oxygen saturation corresponding to the observation distance is not corrected.

In the endoscope system 10, however, if a setting indicating that a colorant is introduced into the subject is performed in the processor device 16, an observation distance is calculated in the second measurement mode for coloring, and the oxygen saturation is corrected based on the accurate observation distance calculated in the second measurement mode. Therefore, even if the specific tissue 111 is colored, for example, as in an oxygen saturation image 116, a correct low oxygen region 102 is displayed as in the oxygen saturation image 101. In addition, even in a case in which the low oxygen region 102 is magnified by bringing the distal portion 24 close to the subject (or by performing a zooming operation) to shorten the observation distance, the second measurement mode for coloring is calculated, and the oxygen saturation is corrected based on the accurate observation distance calculated in the second measurement mode. Therefore, as in an oxygen saturation image 118, even if the specific tissue 111 is colored, it is possible to correctly magnify and observe a region around the low oxygen region 102 without the artifact 104 appearing unlike in the oxygen saturation image 105.

The display of such oxygen saturation (oxygen saturation image) is continuously performed until switching to the normal observation mode occurs (S21). In the case of ending the diagnosis, the insertion unit 21 of the endoscope 12 is extracted from the subject (S22).

As described above, the endoscope system 10 measures the observation distance based on the image signals obtained from the image sensor 48. For this reason, it is not necessary to add an interferometer or the like for measuring the observation distance. Therefore, low-cost production is possible, and the degree of freedom in design is not reduced.

As observation distance measurement modes, there are the first measurement mode, in which the observation distance is calculated in a case in which no colorant is present in the subject, and the second measurement mode, in which the observation distance is calculated in a case in which a colorant is present in the subject. Accordingly, in the case of introducing a colorant into the subject, the observation distance is measured in the second measurement mode that is suitable in a case in which a colorant is introduced. Therefore, even if a specific tissue is colored by the introduction of a colorant and the balance of the image signals of the respective colors is lost compared with a normal case in which no colorant is introduced, the endoscope system 10 can calculate the observation distance accurately.

The endoscope system 10 corrects the oxygen saturation based on the high-accuracy observation distance, and generates and displays an oxygen saturation image using the corrected oxygen saturation. Accordingly, even if the balance of the image signals of the respective colors is lost due to the presence of a tissue colored with a colorant compared with a normal case in which no colorant is introduced, it is possible to generate and display an accurate oxygen saturation image.

In the normal distance table 83a and the coloring distance table 83b for calculating the observation distance, the amplitude differences ΔBG, ΔGR, and ΔRB and the observation distances corresponding thereto are stored. However, all of the amplitude differences ΔBG, ΔGR, and ΔRB do not necessarily need to be used, and it is possible to calculate an accurate observation distance as in the first embodiment by using one or more of the amplitude differences ΔBG, ΔGR, and ΔRB. For example, only the amplitude difference ΔBG (balance of blurriness between the B1 image signal and the G2 image signal) and the corresponding observation distance may be used.

In the embodiment described above, the distance tables 83a and 83b are used in which the differences ΔBG, ΔGR, and ΔRB between the amplitudes of the specific frequency $\Omega_v$ components of the B1 image signal, the G2 image signal, and the R2 image signal are associated with each other. However, instead of the differences ΔBG, ΔGR, and ΔRB between the amplitudes of the specific frequency $\Omega_v$ components of the B1 image signal, the G2 image signal, and the R2 image signal, the ratio of the amplitudes of the specific frequency $\Omega_v$ components may be used. In addition, although the frequency of the superficial blood vessel is set to the specific frequency $\Omega_v$ in the embodiment described above, a frequency of any kind of tissue may be set to the specific frequency.

In addition, in the embodiment described above, the magnified observation of the low oxygen region 102 is performed after the low oxygen region 102 is confirmed in a long-distance view. However, even if the low oxygen region 102 is not detected in the oxygen saturation image of the long-distance view, magnified observation may be performed. In this case, a low oxygen region may be observed first by the magnified observation. However, the endoscope system 10 calculates an accurate observation distance, and corrects the oxygen saturation according to the calculated accurate observation distance. Therefore, even if a low oxygen region is observed first by the magnified observation, it is possible to calculate and display the accurate oxygen saturation.

In addition, in the embodiment described above, the observation distance is calculated using the normal distance table 83a or the coloring distance table 83b. However, instead of the data of such a table format, a function that associates the frequency component information with the observation distance may be used. For example, a first distance calculation function for the first measurement mode corresponding to the normal distance table 83a and a second distance calculation function for the second measurement mode corresponding to the coloring distance table 83b may be prepared in advance instead of the distance tables 83a and 83b, and the observation distance may be calculated by computation. These functions can be generated from the normal distance table 83a or the coloring distance table 83b. This is the same for the normal error table 87a or the coloring error table 87b used for the correction of oxygen saturation, and corresponding functions may be stored instead of these tables.

In the embodiment described above, the frequency component information extraction section 81 extracts the amplitudes of specific frequency components from the B1 image signal, the G2 image signal, and the R2 image signal as frequency component information. However, for example, the amplitudes of frequency bands having specific widths may be extracted instead of extracting the amplitudes of specific frequency components, and the sum value may be used as frequency component information. A phase may be added in addition to the amplitude, or only the information of a phase may be used. That is, any frequency component information that the frequency component information extraction section 81 extracts from the B1 image signal, the G2 image signal, and the R2 image signal can be used as long as this is information regarding a specific frequency component that can be associated with the observation distance.

In the embodiment described above, the frequency component information extraction section 81 extracts frequency component information (amplitudes of specific frequency components) by performing a Fourier transform of the B1 image signal, the G2 image signal, and the R2 image signal. However, instead of performing the Fourier transform, the frequency component information may also be extracted from the B1 image signal, the G2 image signal, and the R2 image signal using an image filter (two-dimensional filter) that extracts a specific frequency component. Needless to say, frequency component information may be extracted using any method other than the method based on the Fourier transform or the image filter as long as it is possible to extract the frequency component information. The point that any kind of such frequency component information extracted by the frequency component information extraction section 81 or any method of extracting the frequency component information is the same for other embodiments or modifications to be described later.

In the embodiment described above, in the case of introducing a colorant into the subject, the observation distance is measured in the second measurement mode. However, there is a plurality of types of colorants used in the case of observing the subject in the endoscope system 10. In addition, a tissue to be colored or the color differs depending on the type of the colorant. Therefore, although one coloring distance table 83b and one coloring error table 87b are illustrated in the first embodiment described above, it is preferable to provide a plurality of coloring distance tables and a plurality of coloring error tables for each type of colorant (for each combination in a case in which a plurality of colorants are used). In this manner, even if any kind of colorant is used, it is possible to accurately calculate the observation distance and to calculate and display the accurate oxygen saturation in the endoscope system 10.

In addition, in the embodiment described above, a colorant is introduced into the subject. However, even if a colorant is not introduced, the balance of the image signals of the respective colors may be lost compared with the normal observation. Accordingly, the observation distance or the oxygen saturation may not be calculated correctly. For example, a cleaning solution (cleaning agent) for cleaning the inside of the subject is usually colored in order to prevent accidental ingestion or the like. For this reason, if the cleaning solution remains in the subject, the balance of the image signals of the respective colors is lost as in the case in which a colorant is introduced. As a result, the observation distance or the oxygen saturation is not calculated correctly. Therefore, it is preferable to provide a distance table or an error table corresponding to the remaining of the cleaning solution or the like. In a case in which the presence of the cleaning solution or the like is confirmed, it is possible to calculate the accurate observation distance and oxygen saturation by performing a setting to the measurement mode in which the distance table and the error table are used.

In the embodiment described above, the case in which the balance of the image signals of the respective colors is lost by the introduction of non-hemoglobin substances, such as a colorant that is not present naturally in the subject, and the observation distance or the oxygen saturation is not correctly calculated is illustrated as an example. However, there is also a case in which the balance of the image signals of the respective colors is lost by non-hemoglobin substances that may be present naturally in the subject and the observation distance or the oxygen saturation is not correctly calculated. For example, if residues or the like (feces or feces juice, other colored secretions, or the like) that could not be removed with a cleaning solution are present in the subject, the balance of the image signals of the respective colors is lost. For this reason, the observation distance or the oxygen saturation is not correctly calculated. Therefore, it is preferable to provide a distance table or an error table corresponding to residues or the like that may be present naturally in the subject. In a case in which the presence of residues or the like is confirmed, it is possible to calculate the accurate observation distance and oxygen saturation by performing a setting to the measurement mode in which the distance table and the error table are used.

In addition, the subject at the time of normal observation is observed mainly in the contrast of the image signal of each color corresponding to the amount of absorption (or the amount of reflection) of hemoglobin contained in the blood. In contrast, all of the above-described colorant, cleaning solution, and residues, are substances that break the balance of the contrasts of the image signals of the respective colors corresponding to the amount of absorption (amount of reflection) of hemoglobin. In this specification, substances other than hemoglobin that breaks the balance of the contrasts of the image signals of the respective colors are referred to collectively as a non-hemoglobin substance.

In the embodiment described above, the observation distance is measured in the special observation mode, and the oxygen saturation is corrected based on the calculated observation distance. However, also in the normal observation mode in which no oxygen saturation is calculated, the observation distance may be measured by the observation distance measurement unit 63. By displaying the observation distance calculated in the normal observation mode on the monitor 18 together with the normal image, it is possible to assist a safe operation so that the subject is not damaged by the distal portion 24.

Although the measurement of the observation distance in the normal observation mode can be performed in the same manner as in the embodiment described above, it is possible to calculate the observation distance using the image signals of R, and B colors, which are output in one frame by the image sensor 48, in the measurement of the observation distance in the observation mode. That is, it is possible to measure the accurate observation distance just with image signals obtained in only one frame.

In the embodiment described above, the B1 image signal, the G2 image signal, and the R2 image signal that are used for the calculation of oxygen saturation are used in the measurement of the observation distance in the special observation mode. However, the measurement of the observation distance may be performed using the B1 image signal, the G1 image signal, and the R1 image signal obtained in the first frame, or the measurement of the observation distance may be performed using the B2 image signal, the G2 image signal, and the R2 image signal obtained in the second frame. In this manner, also in the special observation mode, it is possible to measure the accurate observation distance just with image signals obtained in only one frame as in the measurement of the observation distance in the normal observation mode.

In addition, in the embodiment described above, oxygen saturation is calculated based on the signal ratio B1/G2 and the signal ratio R2/G2, and correction processing is performed on the data of the calculated oxygen saturation. However, image signals used for the calculation of oxygen saturation may be corrected according to the observation distance, and the oxygen saturation may be calculated using the corrected image signal.

In the endoscope system 10, the phosphor 44 is provided in the distal portion 24 of the endoscope 12. However, the phosphor 44 may be provided in the light source device 14 instead. In this case, the phosphor 44 is provided between the first blue laser light source (473 LD) 34 and the second blue laser light source (445 LD) 36 and the light guide 41. The first blue laser light source 34 or the second blue laser light source 36 is made to emit the first blue laser light or the second blue laser light is to the phosphor 44. Accordingly, the first white light or the second white light is emitted. The first or second white light is emitted to the inside of the subject through the light guide 41. Other than these, the above is the same as the endoscope system 10.

In addition, although the first and second blue laser light beams are incident on the same phosphor 44, the first blue laser light and the second blue laser light may be respectively incident on the first phosphor and the second phosphor.

Second Embodiment

Figure 25:
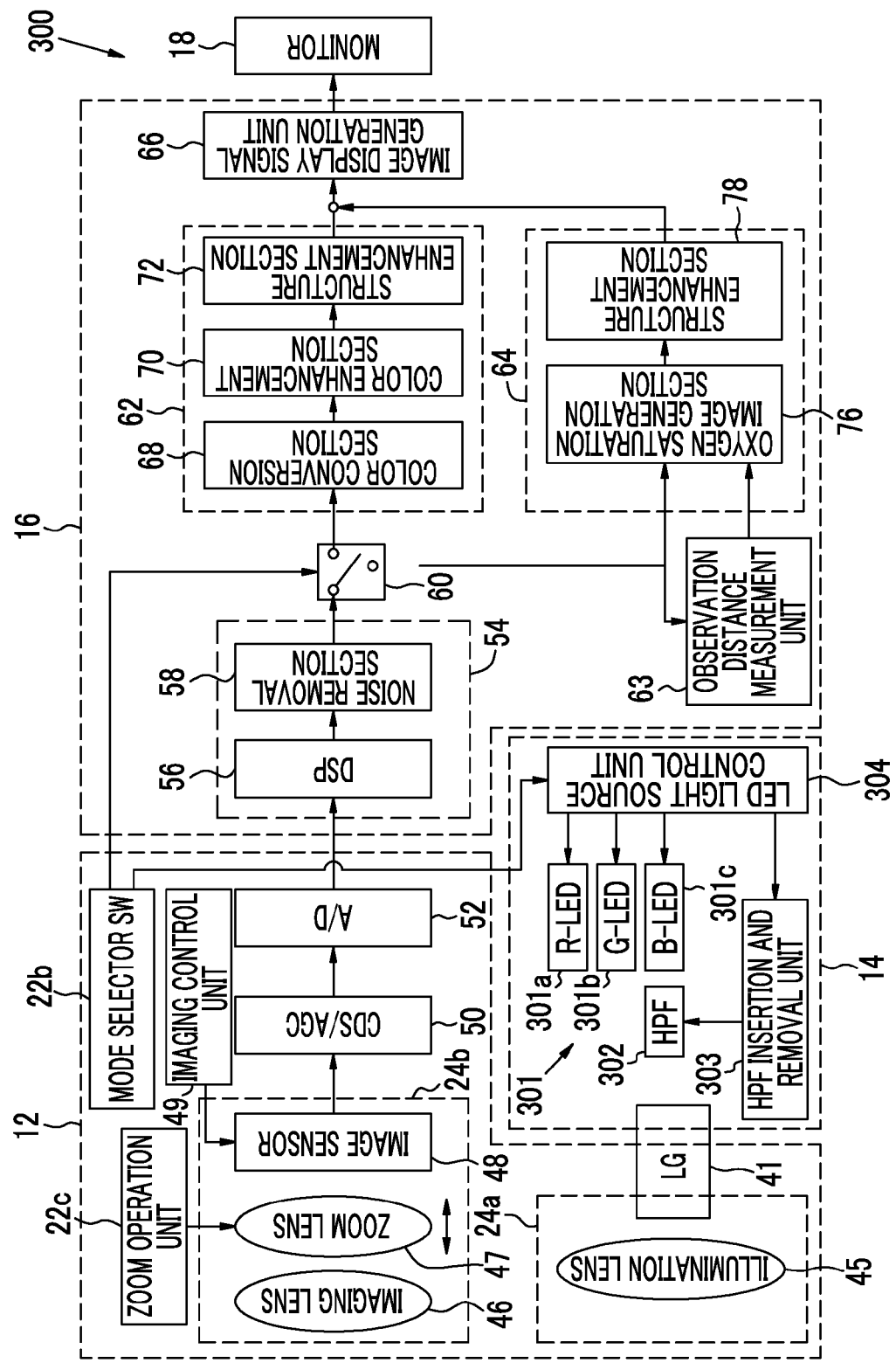
FIG. 25 is a block diagram of an endoscope system of a second embodiment.

As shown in FIG. 25, in a light source device 14 of an endoscope system 300, a light emitting diode (LED) light source unit 301 and an LED light source control unit 304 are provided instead of the first and second blue laser light sources 34 and 36 and the light source control unit 40. In addition, the phosphor 44 is not provided in an illumination optical system 24a of the endoscope system 300. Other than these, the endoscope system 300 is the same as the endoscope system 10 of the first embodiment.

Figure 26:
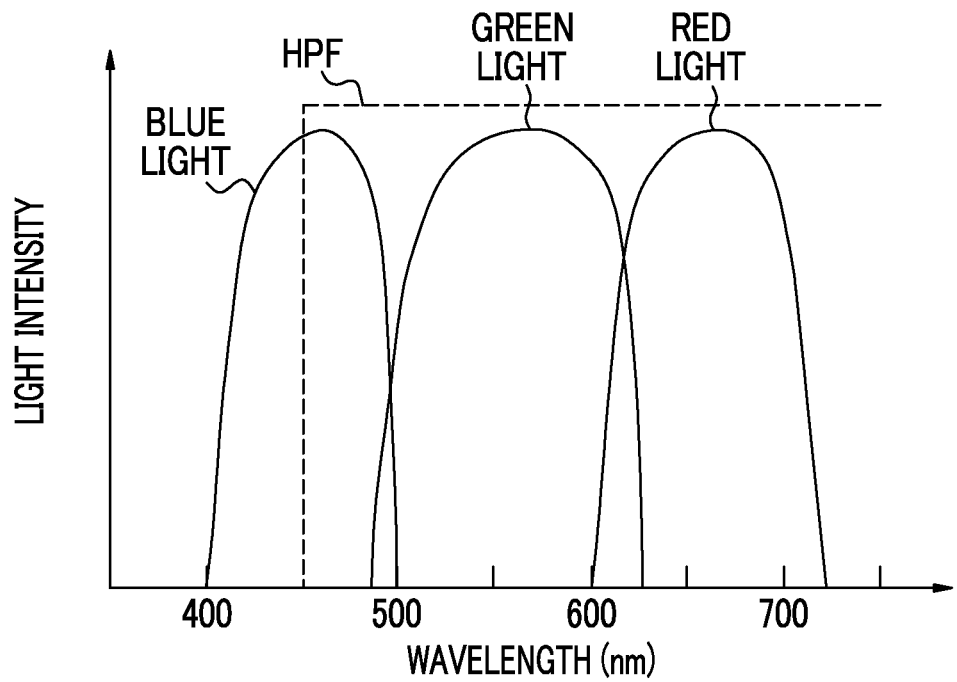
FIG. 26 is a graph showing the light emission band of an LED and the characteristics of an HPF.

The LED light source unit 301 includes an R-LED 301a, a G-LED 301b, and a B-LED 301c as light sources for emitting light limited to a specific wavelength band. As shown in FIG. 26, the R-LED 301a emits red band light (hereinafter, simply referred to as red light) in a red region of 600 nm to 720 nm, and the G-LED 301b emits green band light (hereinafter, simply referred to as green light) in a green region of 480 nm to 620 nm. The B-LED 301c emits blue band light (hereinafter, simply referred to as blue light) in a blue region of 400 nm to 500 nm.

The LED light source unit 301 includes a high pass filter (HPF) 302 that is removably inserted on the optical path of the blue light emitted from the B-LED 301c. The high pass filter 302 cuts blue light in a wavelength band of 450 nm or less, and allows light in a wavelength band higher than 450 nm to be transmitted therethrough.

The cutoff wavelength (450 nm) of the high pass filter 302 is a wavelength at which the absorption coefficient of oxygenated hemoglobin and the absorption coefficient of reduced hemoglobin are almost equal (refer to FIG. 16), and the absorption coefficient of oxygenated hemoglobin and the absorption coefficient of reduced hemoglobin are reversed in the order of magnitude with the cutoff wavelength as a boundary. In the present embodiment, the correlation stored in the correlation storage section 85 is that the absorption coefficient of oxygenated hemoglobin is larger than the absorption coefficient of reduced hemoglobin. Accordingly, in a signal based on the wavelength band equal to or lower than the cutoff wavelength, the signal ratio B1/G2 is lower than the original value measured at 473 nm. This is a cause of calculating incorrect oxygen saturation. For this reason, when acquiring the B1 image signal for calculating the oxygen saturation, the high pass filter 302 blocks light in a wavelength band equal to or lower than the cutoff wavelength from being emitted to the subject.

Accordingly, the high pass filter 302 is inserted before the B-LED 301c in the special observation mode, and is retracted to the retraction position in the normal observation mode. The insertion and removal of the high pass filter 302 are performed by an HPF insertion and removal unit 303 under the control of the LED light source control unit 304.

Figure 27:
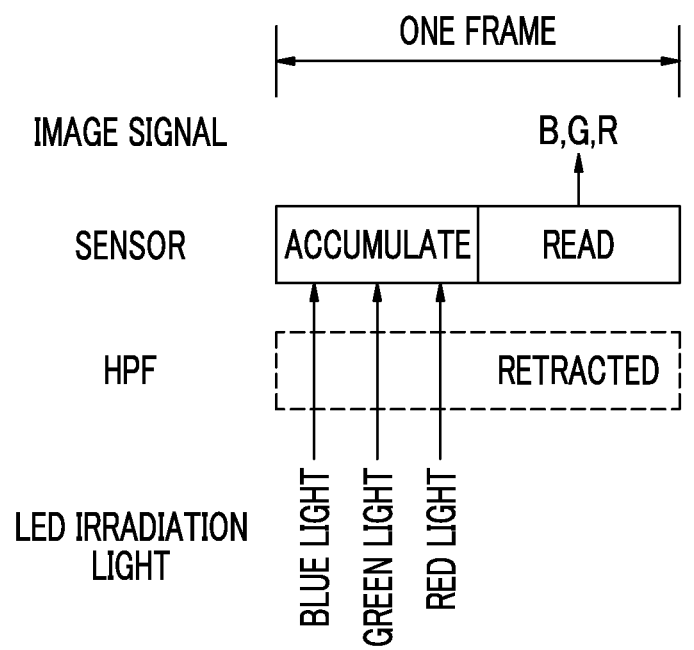
FIG. 27 is an explanatory diagram showing imaging control in the normal observation mode in the second embodiment.

The LED light source control unit 304 controls ON/OFF of the LEDs 301a to 301c of the LED light source unit 301 and the insertion and removal of the high pass filter 302. Specifically, as shown in FIG. 27, in the normal observation mode, the LED light source control unit 304 turns on all of the LEDs 301a to 301c and retracts the high pass filter 302 from the optical path of the B-LED 301c.

Figure 28:
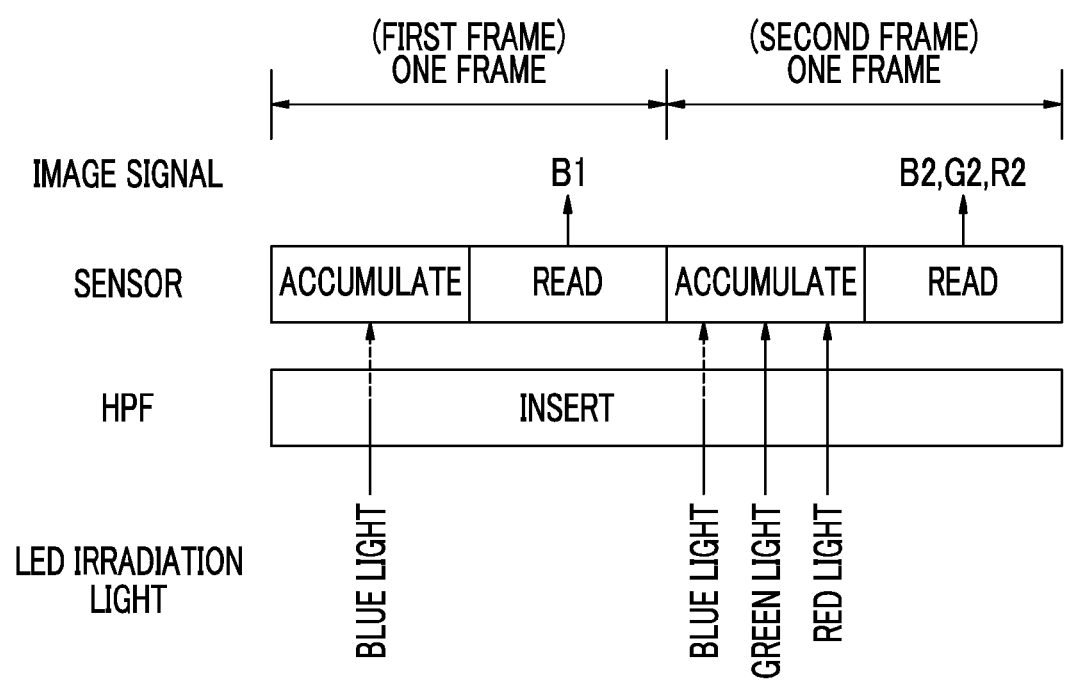
FIG. 28 is an explanatory view showing imaging control in the special observation mode in the second embodiment.

On the other hand, as shown in FIG. 28, in the special observation mode, the LED light source control unit 304 inserts the high pass filter 302 on the optical path of the B-LED 301c. Then, in the first frame, the B-LED 301c is turned on and the R-LED 301a and the G-LED 301b are turned off, so that blue light in which a wavelength band equal to or lower than 450 nm has been cut is emitted to the inside of the subject. Then, in the second frame, all of the R-LED 301a, the G-LED 301b, and the B-LED 301c are turned on, so that white light configured to include blue light obtained by cutting a wavelength band equal to or lower than 450 nm from the blue light emitted from the B-LED 301c, red light emitted from the R-LED 301a, and green light emitted from the G-LED 301b is emitted to the inside of the subject. In this manner, the image sensor 48 outputs the B1 image signal in the first frame, and outputs the R2 image signal, the G2 image signal, and the B2 image signal in the second frame. Accordingly, subsequent processing can be performed in the same manner as in the endoscope system 10 of the first embodiment.

In the present embodiment, in both the first and second frames in the special observation mode, the subject is imaged in a state in which the high pass filter 302 is inserted. However, the high pass filter 302 may be inserted only in the first frame, and the high pass filter 302 may be removed in the second frame. In addition, in the first frame in the special observation mode, only the B-LED 301c is turned on to emit only the blue light to the subject. However, also in the first frame, the R-LED 301a and the G-LED 301b may be turned on to output the R1 image signal and the G1 image signal to the image sensor 48.

Third Embodiment

Figure 29:
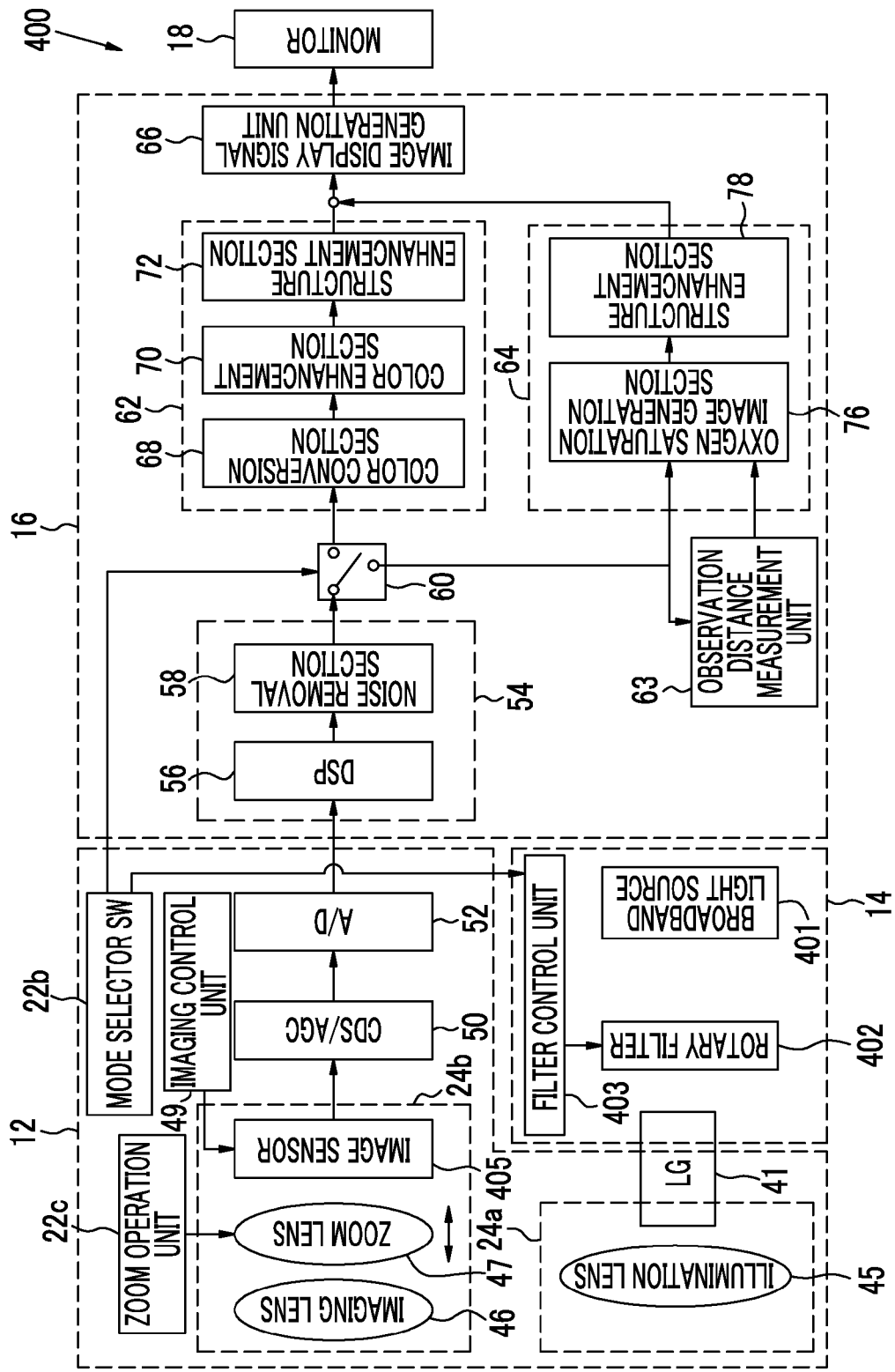
FIG. 29 is a block diagram of an endoscope system of a third embodiment.

As shown in FIG. 29, in a light source device 14 of an endoscope system 400, a broadband light source 401, a rotary filter 402, and a rotary filter control unit 403 are provided instead of the first and second blue laser light source 34 and 36 and the light source control unit 40. An image sensor 405 of the endoscope system 400 is a monochrome imaging device in which no color filter is provided. Other than these, the endoscope system 400 is the same as the endoscope systems of the first to third embodiments.

The broadband light source 401 is, for example, a xenon lamp or a white LED, and emits white light having a wavelength in a wavelength band ranging from blue to red. The rotary filter 402 includes a normal observation mode filter 410 and a special observation mode filter 411 (refer to FIG. 30), and can move in a radial direction between a first position for normal observation mode to place the normal observation mode filter 410 on the optical path, in which the white light emitted from the broadband light source 401 is incident on the light guide 41, and a second position for special observation mode to place the special observation mode filter 411 on the optical path. The movement of the rotary filter 402 to the first and second positions is controlled by the rotary filter control unit 403 according to the selected observation mode. In addition, the rotary filter 402 rotates according to the imaging frame of the image sensor 405 in a state of being placed at the first or second position. The rotation speed of the rotary filter 402 is controlled by the rotary filter control unit 403 according to the selected observation mode.

Figure 30:
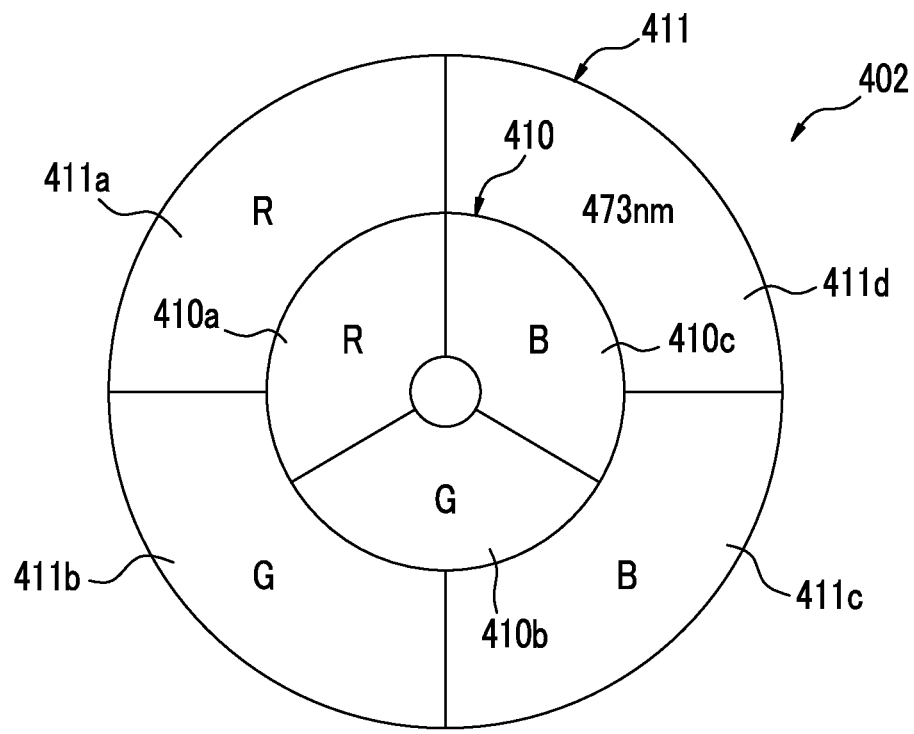
FIG. 30 is a plan view of a rotary filter.

As shown in FIG. 30, the normal observation mode filter 410 is provided in the inner peripheral portion of the rotary filter 402. The normal observation mode filter 410 includes an R filter 410a that transmits red light, a G filter 410b that transmits green light, and a B filter 410c that transmits blue light. Therefore, when the rotary filter 402 is placed at the first position for normal light observation mode, the white light from the broadband light source 401 is incident on one of the R filter 410a, the G filter 410b, and the B filter 410c according to the rotation of the rotary filter 402. As a result, red light, green light, and blue light are sequentially emitted to the subject according to the transmitted filter, and the image sensor 405 sequentially outputs an R image signal, a G image signal, and a B image signal by imaging the subject by receiving the reflected light of the red light, the green light, and the blue light.

The special observation mode filter 411 is provided in the outer peripheral portion of the rotary filter 402. The special observation mode filter 411 includes an R filter 411a that transmits red light, a G filter 411b that transmits green light, a B filter 411c that transmits blue light, and a narrowband filter 411d that transmits narrowband light of 473±10 nm. Therefore, when the rotary filter 402 is placed at the second position for normal light observation mode, the white light from the broadband light source 401 is incident on one of the R filter 411a, the G filter 411b, the B filter 411c, and the narrowband filter 411d according to the rotation of the rotary filter 402. As a result, red light, green light, blue light, and narrowband light (473 nm) are sequentially emitted to the subject according to the transmitted filter, and the image sensor 405 sequentially outputs an R image signal, a G image signal, a B image signal, and a narrowband image signal by imaging the subject by receiving the reflected light of the red light, the green light, the blue light, and the narrowband light.

The R image signal and the G image signal obtained in the special observation mode correspond to the R1 (or R2) image signal and the G1 (or G2) image signal in the first embodiment, respectively. In addition, the B image signal obtained in the special observation mode corresponds to the B2 image signal in the first embodiment, and the narrowband image signal corresponds to the B1 image signal. Accordingly, subsequent processing can be performed in the same manner as in the endoscope systems of the first to third embodiments.

Figure 31:
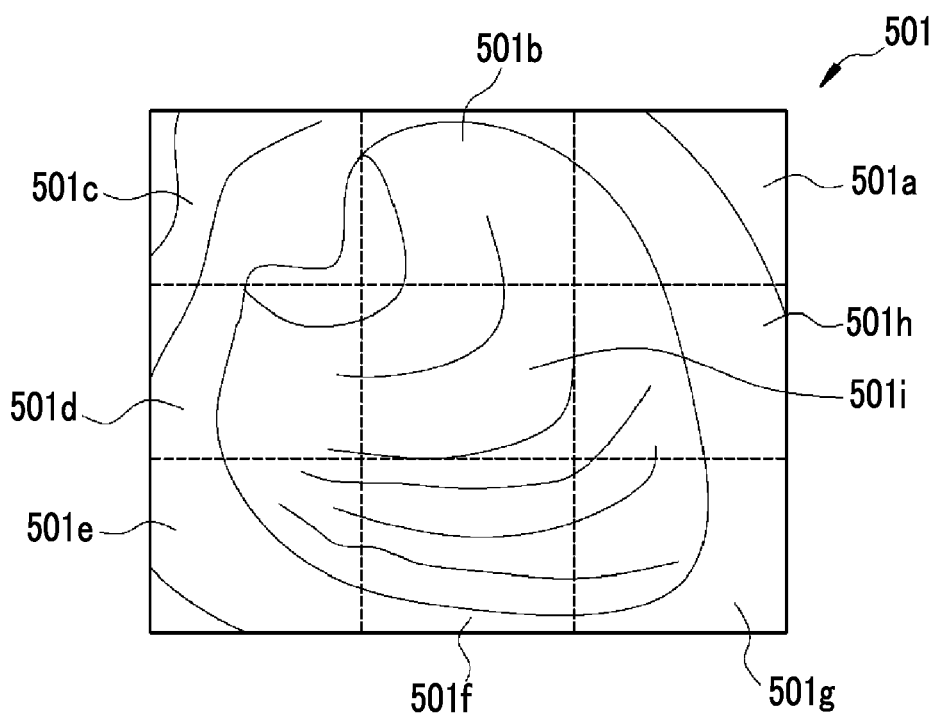
FIG. 31 is an explanatory diagram showing divided regions.

In the first to third embodiments (particularly, the first and second embodiments), the measurement of the observation distance and the correction of the error of the oxygen saturation corresponding to the measured observation distance are performed for all image signals. However, the measurement of the observation distance and the correction of the error of the oxygen saturation corresponding to the measured observation distance are preferably performed in each of a plurality of divided regions obtained by dividing the B1 image signal, the G2 image signal, and the R2 image signal. For example, as shown in FIG. 31, a B1 image signal 501 is divided into a total of nine divided regions 501a to 501i of 3×3 in horizontal and vertical directions. Then, in the divided regions 501a to 501i, specific frequency $\Omega_v$ components are extracted, and the amplitude differences ΔBG, ΔGR, and ΔRB are calculated. Then, it is preferable to correct the error of the oxygen saturation or correct the image signals for each of the divided regions 501a to 501i based on the amplitude differences ΔBG, ΔGR, and ΔRB calculated in each of the divided regions 501a to 501i. This is the same for the G2 image signal and the R2 image signal.

Figure 32:
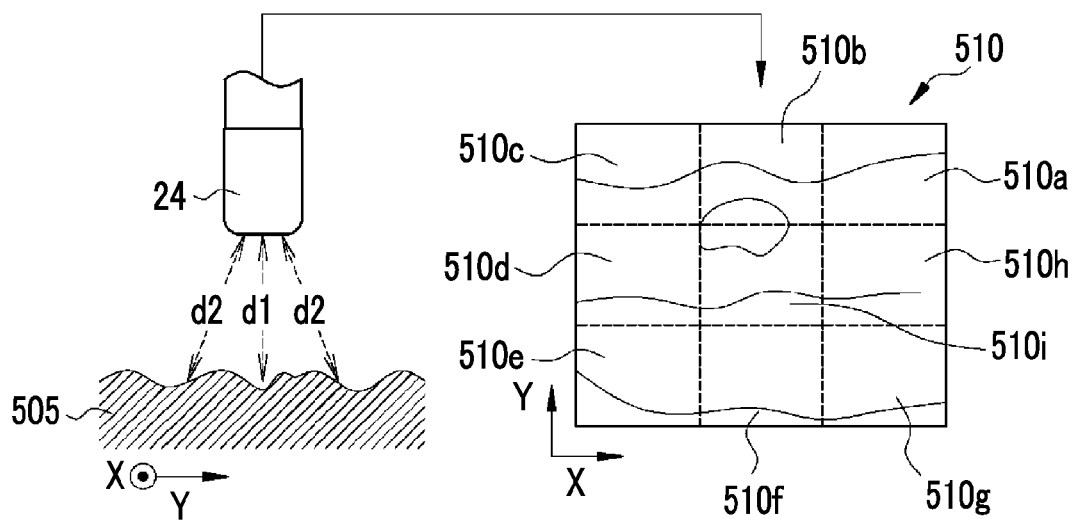
FIG. 32 is an explanatory diagram showing the relationship between the divided region and the observation distance.

Thus, by dividing each of the B1 image signal, the G2 image signal, and the R2 image signal into a plurality of divided regions 501a to 501i and performing measurement of the observation distance and correction of the error of the oxygen saturation in each of the divided regions 501a to 501i, the accuracy of measurement and correction is improved. For example, as shown in FIG. 32, in the case of performing observation by capturing a subject 505 (for example, a lumen wall) at the front in the distal portion 24, it is assumed that the distance (observation distance) between the distal portion 24 and the subject 505 projected to the central divided regions 510i among the divided regions obtained by dividing an image signal 510 into nine parts is d1. Then, in the other divided regions 510a to 510h, the distance between the distal portion 24 and each part of the subject 505 corresponding to each of the divided regions 501a to 510h is d2 (d2>d1). Accordingly, the observation distance is longer than the central divided region 510i.

For this reason, when the Fourier transform of the entire image signal 510 is collectively performed to extract the amplitudes of the specific frequency $\Omega_v$ components and the amplitude differences ΔBG, ΔGR, and ΔRB are calculated, the amplitude differences ΔBG, ΔGR, and ΔRB in the central divided regions 510i become different values from the amplitude differences ΔBG, ΔGR, and ΔRB in the surrounding divided regions 510a to 510h. In addition, as the zoom magnification increases or as the distal portion 24 becomes close to the subject 505, the differences become noticeable. Accordingly, if the measurement of the observation distance and the correction of the error of the oxygen saturation are performed similarly in all of the divided regions 510a to 501i, an error occurs in the central divided region 510i or the surrounding divided regions 510a to 510h or in both the central divided region 510i and the surrounding divided regions 510a to 510h. On the other hand, by correcting the error of the oxygen saturation or correcting the image signal for each of the divided regions 510a to 510i, it is possible to perform accurate correction in each region.

Figure 33:
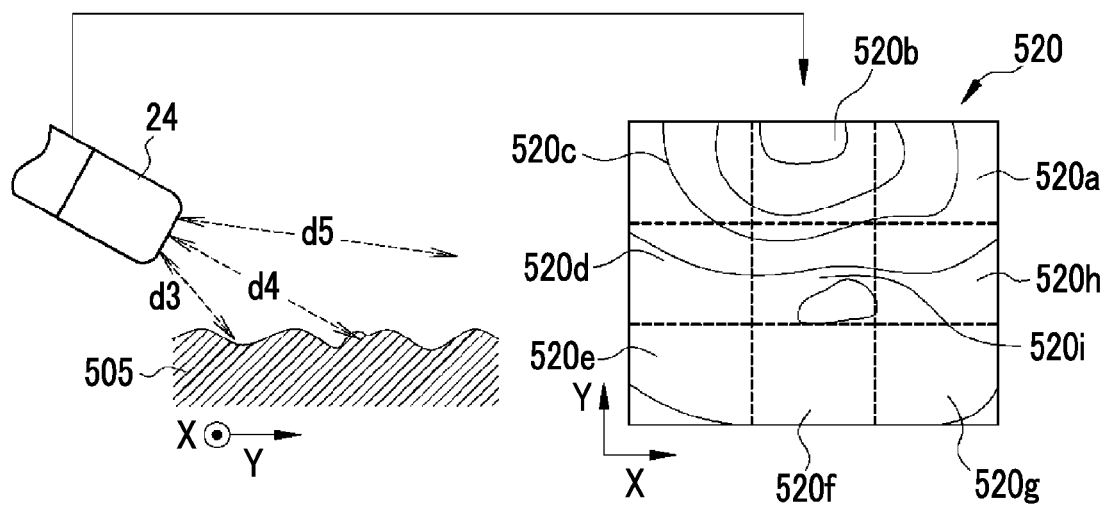
FIG. 33 is an explanatory diagram showing the relationship between the divided region and the observation distance.

As shown in FIG. 33, in the case of observing the subject 505 in a state in which the distal portion 24 is nearly parallel to the subject 505, each observation distance difference between the divided regions 520a to 520i in the obtained image signal 520 is further increased. For example, in the lower three divided regions 520e to 520g of the image signal 520, the distance between the distal portion 24 and the subject 505 is d3 which is the shortest. However, in the middle three divided regions 520d, 520i, and 520h, the distance between the distal portion 24 and the subject 505 is d4 which is longer than d3. In addition, in the upper three divided regions 520a to 520c, the distance between the distal portion 24 and the subject 505 is d5 which is the longest (d3<d4<d5). in a case in which the difference between the observation distances in the image signal 520 is large as described above, if the amplitude differences ΔBG, ΔGR, and ΔRB are collectively calculated for the entire image signal 520 (all of the divided regions 520a to 520i), correction of the error of the oxygen saturation is likely to be inaccurate. However, by performing the correction in each of the divided regions 520a to 520i, it is possible to correct the error of the oxygen saturation or correct the image signals more accurately than in the case of performing correction collectively for the entire image signal 520.

In addition, although the image signal is divided into nine divided regions of 3×3 and the correction of the error of the oxygen saturation or the correction of the image signal is performed in each of the divided regions in FIGS. 31 to 33, the number of divided regions is arbitrary. The correction accuracy is improved as the number of divisions increases, but a time for the correction processing is required. Therefore, in order to make the correction processing speed and the correction accuracy compatible with each other, it is preferable to divide the image signal into a total of about nine regions of 3×3 as described above.

Although the oxygen saturation is calculated based on the signal ratio B1/G2 and the signal ratio R2/G2 in the first to third embodiments, it is also possible to calculate the oxygen saturation based on only the signal ratio B1/G2. In this case, it is preferable to store the correlation between the signal ratio B1/G2 and the oxygen saturation in the correlation storage section 85.

Although the oxygen saturation image obtained by imaging the oxygen saturation is generated and displayed in the first to third embodiments, a blood volume image obtained by imaging the blood volume may be generated and displayed in addition to the generation and display of the oxygen saturation image. Since the blood volume is correlated with the signal ratio R2/G2, a blood volume image obtained by imaging the blood volume can be generated by assigning different colors according to the signal ratio R2/G2.

In the first to third embodiments, the oxygen saturation is calculated. However, instead of or in addition to the oxygen saturation, other kinds of biological function information, such as an oxygenated hemoglobin index that is calculated from "blood volume (signal ratio R2/G2)×oxygen saturation (%)" or a reduced hemoglobin index that is calculated from "blood volume×(1−oxygen saturation) (%)", may be calculated.

EXPLANATION OF REFERENCES 10, 300, 400: endoscope system
63: observation distance measurement unit
76: oxygen saturation image generation section
81: frequency information extraction section
82: difference calculation section
83: observation distance calculation section
87: correction section

What is claimed is:

1. An endoscope system, comprising:
a light source device that emits signal light, which has a wavelength band absorbed by hemoglobin contained in a subject, to the subject;
an endoscope having an image sensor that images the subject by receiving reflected light of the signal light and outputs image signals of a plurality of colors; and
an observation distance measurement unit that measures an observation distance that is a distance between a distal portion of the endoscope and the subject based on the image signals of the plurality of colors,
wherein the observation distance measurement unit includes a frequency component information extraction section that performs a fourier transform on the image signals of the plurality of colors and extracts amplitudes of a specific frequency component of the plurality of colors and an observation distance calculation section that calculates the observation distance based on a difference between the amplitudes of the specific frequency component extracted for two image signals having different corresponding wavelength bands.

2. The endoscope system according to claim 1,
wherein the observation distance measurement unit is means for measuring the observation distance based on the image signal, is capable of performing switching between a first measurement mode to measure the observation distance in a case in which a non-hemoglobin substance that changes an amount of reflection of the signal light by the subject is not present other than hemoglobin contained in the subject and a second measurement mode to measure the observation distance in a case in which the non-hemoglobin substance is present, and calculates the observation distance in one of the first and second measurement modes.

3. The endoscope system according to claim 1,
wherein the specific frequency component is information regarding a frequency component corresponding to a superficial blood vessel of the subject.

4. The endoscope system according to claim 2,
wherein the observation distance calculation section has a first distance table, in which the frequency component information in a case in which the non-hemoglobin substance is not present is associated with the observation distance, and a second distance table, in which the frequency component information in a case in which the non-hemoglobin substance is present is associated with the observation distance, and calculates the observation distance using the first distance table in the first measurement mode and using the second distance table in the second measurement mode.

5. The endoscope system according to claim 1,
wherein the observation distance calculation section has a first distance table, in which the frequency component information in a case in which the non-hemoglobin substance is not present is associated with the observation distance, and a second distance table, in which the frequency component information in a case in which the non-hemoglobin substance is present is associated with the observation distance, and calculates the observation distance using the first distance table in the first measurement mode and using the second distance table in the second measurement mode.

6. The endoscope system according to claim 2, wherein the observation distance calculation section calculates the observation distance using a function of associating the amplitudes of the specific frequency component of the plurality of colors with the observation distance, and has a first distance calculation function for the first measurement mode and a second distance calculation function for the second measurement mode as the function.

7. The endoscope system according to claim 2, further comprising:
a non-hemoglobin substance introduction unit that introduces the non-hemoglobin substance.

8. The endoscope system according to claim 2, wherein the non-hemoglobin substance is a colorant for coloring the subject and/or a cleaning agent for cleaning an inside of the subject.

9. The endoscope system according to claim 8, wherein the colorant contains at least one of indigo carmine, toluidine blue, methylene blue, compound iodine glycerin, crystal violet, fluorescein, acridine orange, indocyanine green, and acetic acid.

10. The endoscope system according to claim 2, wherein the non-hemoglobin substance is residues remaining in the subject and/or secretions secreted by the subject.

11. The endoscope system according to claim 1, wherein the endoscope includes a zoom lens for magnifying an image that is formed on the image sensor by the reflected light of the signal light, and
the observation distance is a distance based on a magnification of the image by the zoom lens.

12. The endoscope system according to claim 1, wherein the observation distance calculation section divides the image signal into a plurality of regions, and calculates the observation distance for each of the regions.

13. The endoscope system according to claim 1, wherein the light source device emits first signal light and second signal light having different wavelength bands to the subject as the signal light,
the image sensor images the subject by receiving reflected light of the first signal light and reflected light of the second signal light, and outputs a first image signal and a second image signal, and
the endoscope system further comprising:
an oxygen saturation calculation unit that calculates an oxygen saturation of the subject for each pixel based on a signal ratio between the first image signal and the second image signal output from the same pixel;
a correction unit that corrects the oxygen saturation based on the observation distance; and
an image generation unit that generates an oxygen saturation image showing the oxygen saturation of the subject based on the oxygen saturation corrected by the correction unit.

14. A processor device for an endoscope system according to claim 1 including the light source device that emits signal light, which has the wavelength band absorbed by hemoglobin contained in the subject, to the subject, and the endoscope having the image sensor that images the subject by receiving reflected light of the signal light and outputs the image signals of the plurality of colors, the processor device comprising:
the observation distance measurement unit that measures the observation distance that is the distance between the distal portion of the endoscope and the subject based on the image signals of the plurality of colors,
wherein the observation distance measurement unit includes the frequency component information extraction section that performs the fourier transform on the image signals of the plurality of colors and extracts the amplitudes of the specific frequency component of the plurality of colors and the observation distance calculation section that calculates the observation distance based on the difference between the amplitudes of the specific frequency component extracted for the two image signals having the different corresponding wavelength bands.

15. An operation method for an endoscope system according to claim 1 including the light source device that emits signal light, which has the wavelength band absorbed by hemoglobin contained in the subject, to the subject, and the endoscope having the image sensor that images the subject by receiving reflected light of the signal light and outputs the image signals of the plurality of colors, the operation method comprising:
an observation distance measurement step of performing the fourier transform on the image signals of the plurality of colors, extracting amplitudes of the specific frequency component of the plurality of colors and measuring the observation distance that is the distance between the distal portion of the endoscope and the subject based on the difference between the amplitudes of the specific frequency component extracted for the two image signals having the different corresponding wavelength bands.

16. A distance measurement device used for an endoscope system according to claim 1, comprising:
the light source device that emits signal light, which has the wavelength band absorbed by hemoglobin contained in the subject, to the subject;
the image sensor that images the subject by receiving reflected light of the signal light and outputs the image signals of the plurality of colors; and
the observation distance measurement unit that measures the observation distance that is the distance between the distal portion of the endoscope and the subject based on the image signals of the plurality of colors,
wherein the observation distance measurement unit includes the frequency component information extraction section that performs the fourier transform on the image signals of the plurality of colors and extracts the amplitudes of the specific frequency component of the plurality of colors and the observation distance calculation section that calculates the observation distance based on the difference between the amplitudes of the specific frequency component extracted for the two image signals having the different corresponding wavelength bands.

17. An endoscope system, comprising:
a light source device that emits signal light, which has a wavelength band absorbed by hemoglobin contained in a subject, to the subject;

an endoscope having an image sensor that images the subject by receiving reflected light of the signal light and outputs image signals of a plurality of colors; and an observation distance measurement unit that measures an observation distance that is a distance between a distal portion of the endoscope and the subject based on the image signals of the plurality of colors, wherein the observation distance measurement unit includes a frequency component information extraction section that extracts amplitudes of a specific frequency component of the plurality of colors from the image signals of the plurality of colors by using an image filter and an observation distance calculation section that calculates the observation distance based on a difference between the amplitudes of the specific frequency component extracted for two image signals having different corresponding wavelength bands.

* * * * *